US010895020B2

(12) United States Patent
Krieger et al.

(10) Patent No.: US 10,895,020 B2
(45) Date of Patent: Jan. 19, 2021

(54) METHOD FOR GENERATING AN ELECTRO SPUN FIBER MEDICAL IMPLANT

(71) Applicants: CHILDREN'S NATIONAL MEDICAL CENTER, Washington, DC (US); RESEARCH INSTITUTE AT NATIONWIDE CHILDREN'S HOSPITAL, Columbus, OH (US); NANOFIBER SOLUTIONS LLC, Wilmington, DE (US)

(72) Inventors: Axel Krieger, Washington, DC (US); Narutoshi Hibino, Towson, MD (US); Jed Johnson, Columbus, OH (US); Justin Opfermann, Washington, DC (US); Carolyn Cochenour Dorgan, Washington, DC (US); Christopher K. Breuer, New Albany, OH (US)

(73) Assignees: CHILDREN'S NATIONAL MEDICAL CENTER, Washington, DC (US); RESEARCH INSTITUTE AT NATIONWIDE CHILDREN'S HOSPITAL, Columbus, OH (US); NANOFIBER SOLUTIONS LLC, Wilmington, DE (US)

( * ) Notice: Subject to any disclaimer, the term of this patent is extended or adjusted under 35 U.S.C. 154(b) by 150 days.

(21) Appl. No.: 15/755,149

(22) PCT Filed: Aug. 26, 2016

(86) PCT No.: PCT/US2016/049080
§ 371 (c)(1),
(2) Date: Feb. 26, 2018

(87) PCT Pub. No.: WO2017/035500
PCT Pub. Date: Mar. 2, 2017

(65) Prior Publication Data
US 2018/0245243 A1  Aug. 30, 2018

Related U.S. Application Data

(60) Provisional application No. 62/209,990, filed on Aug. 26, 2015.

(51) Int. Cl.
*B29C 33/44* (2006.01)
*B29C 33/48* (2006.01)
(Continued)

(52) U.S. Cl.
CPC ............. *D01D 5/0076* (2013.01); *A61F 2/06* (2013.01); *B29C 33/3842* (2013.01);
(Continued)

(58) Field of Classification Search
CPC ....... B22C 9/00; B22D 23/00; B29C 33/3842; B29C 33/44; B29C 33/48; B29C 33/485;
(Continued)

(56) References Cited

U.S. PATENT DOCUMENTS

2002/0125613 A1  9/2002  Cominsky
2011/0000398 A1*  1/2011  Wallen .................... B29C 33/52
106/614
(Continued)

OTHER PUBLICATIONS

International Search Report dated Nov. 4, 2016 in PCT/US2016/049080 filed Aug. 26, 2016.

*Primary Examiner* — Leo B Tentoni
(74) *Attorney, Agent, or Firm* — Oblon, McClelland, Maier & Neustadt, L.L.P.

(57) ABSTRACT

A method for generating a electro spun fiber medical implant including determining dimensions of a portion of anatomy of a patient corresponding to the electro spun fiber medical implant via medical imaging, generating a model of the
(Continued)

portion of the anatomy based on the dimensions, the model including one or more solid areas and one or more void areas encompassed within the one or more solid areas, inverting the model to generate a mandrel model, the mandrel model generated based on the one or more void areas, generating the mandrel based on the mandrel model, the mandrel including at least one electrically conductive material therein, and applying an electro-spinning process to the mandrel to generate the electro spun fiber medical implant which circumscribes the mandrel, wherein the mandrel is removable from within the electro spun fiber medical implant after a disassembly process.

9 Claims, 17 Drawing Sheets

(51) Int. Cl.

| | | |
|---|---|---|
| *B29C 33/52* | (2006.01) | |
| *D01D 5/00* | (2006.01) | |
| *A61F 2/06* | (2013.01) | |
| *B29C 64/106* | (2017.01) | |
| *B29C 64/112* | (2017.01) | |
| *B29C 33/38* | (2006.01) | |
| *B33Y 50/00* | (2015.01) | |
| *B33Y 80/00* | (2015.01) | |
| *B29C 64/386* | (2017.01) | |
| *B29L 31/00* | (2006.01) | |
| *B33Y 10/00* | (2015.01) | |
| *A61B 34/10* | (2016.01) | |

(52) U.S. Cl.
CPC .......... *B29C 33/485* (2013.01); *B29C 64/106* (2017.08); *B29C 64/112* (2017.08); *B29C 64/386* (2017.08); *B33Y 50/00* (2014.12); *B33Y 80/00* (2014.12); *D01D 5/003* (2013.01); *D01D 5/0015* (2013.01); *D01D 5/0023* (2013.01); *D01D 5/0038* (2013.01); *D01D 5/0046* (2013.01); *A61B 34/10* (2016.02); *A61B 2034/105* (2016.02); *A61B 2034/108* (2016.02); *A61F 2240/004* (2013.01); *A61F 2240/008* (2013.01); *B29L 2031/757* (2013.01); *B29L 2031/7532* (2013.01); *B29L 2031/7534* (2013.01); *B33Y 10/00* (2014.12); *D01D 5/0007* (2013.01); *D10B 2331/041* (2013.01); *D10B 2509/06* (2013.01)

(58) Field of Classification Search
CPC ..... B29C 33/52; B29C 64/106; B29C 64/112; B29L 2031/7532; B29L 2031/7534; B29L 2031/757; B33Y 10/00; B33Y 80/00; D01D 5/0015; D01D 5/0023; D01D 5/003; D01D 5/0038; D01D 5/0046; D01D 5/0076; D10B 2509/06
USPC ......... 264/10, 219, 220, 221, 224, 225, 226, 264/227, 308, 317, 464, 465, 466, 484; 164/6, 15, 34, 35, 36
See application file for complete search history.

(56) References Cited

U.S. PATENT DOCUMENTS

| | | | |
|---|---|---|---|
| 2013/0289690 A1* | 10/2013 | Thapliyal | A61F 2/90 264/219 X |
| 2014/0005470 A1* | 1/2014 | Soletti | A61L 27/3625 600/36 |
| 2014/0058194 A1* | 2/2014 | Soletti | A61F 2/062 600/36 |
| 2014/0072951 A1 | 3/2014 | Johnson | |
| 2014/0107803 A1* | 4/2014 | Grosse | C12M 21/08 623/23.72 |
| 2014/0272225 A1 | 9/2014 | Johnson | |
| 2014/0358217 A1 | 12/2014 | Stankus et al. | |
| 2015/0230918 A1 | 8/2015 | Detamore et al. | |

* cited by examiner

STAGE 1
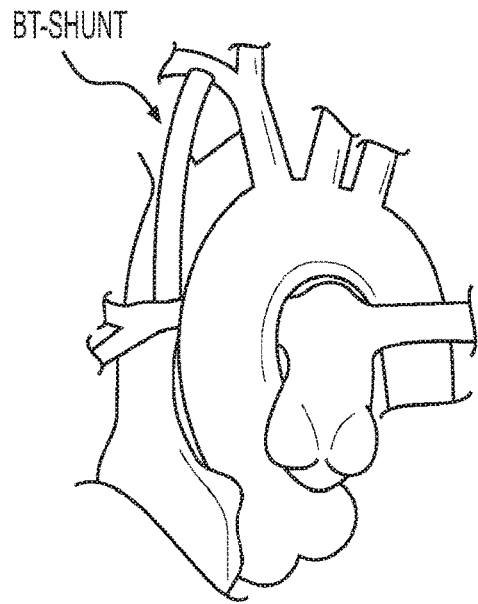
STAGE 2
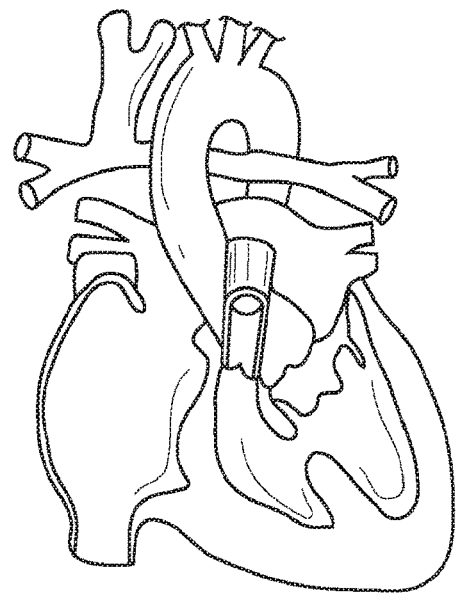
STAGE 3
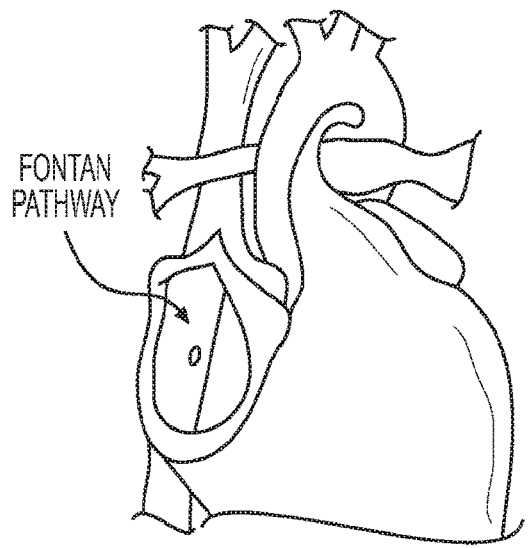
LT FONTAN
STAGE 3
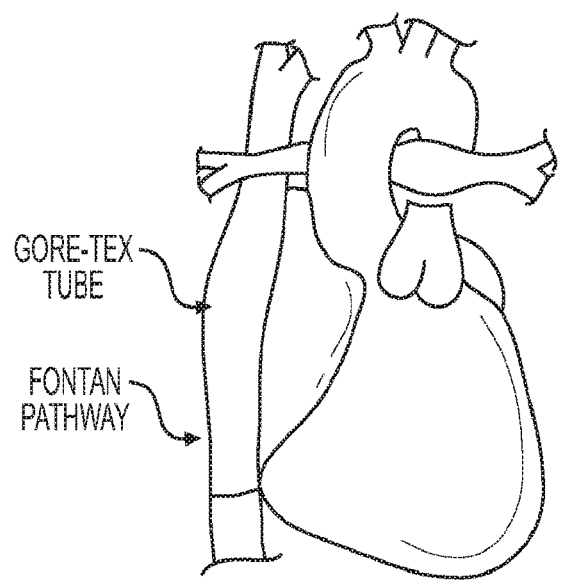
EC FONTAN
FIG. 1

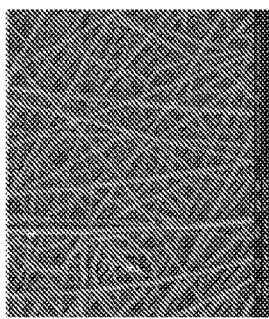
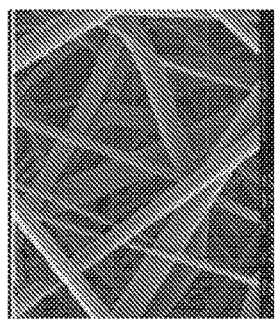
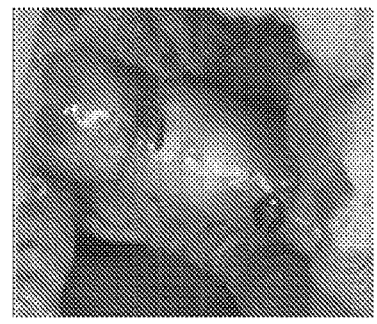
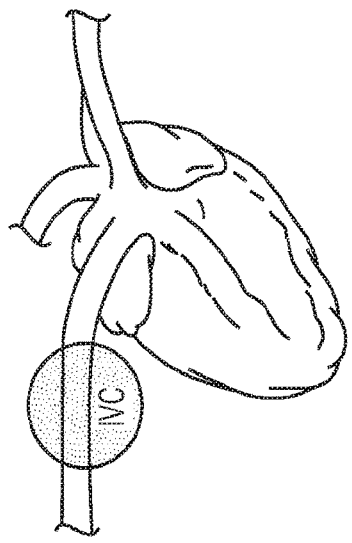
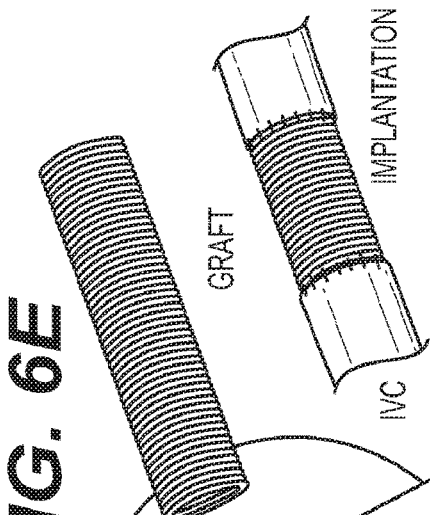
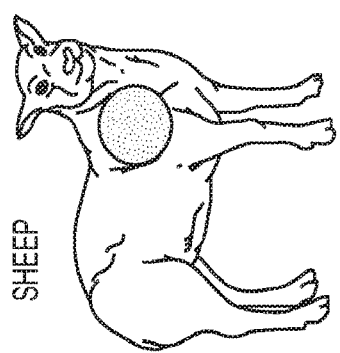
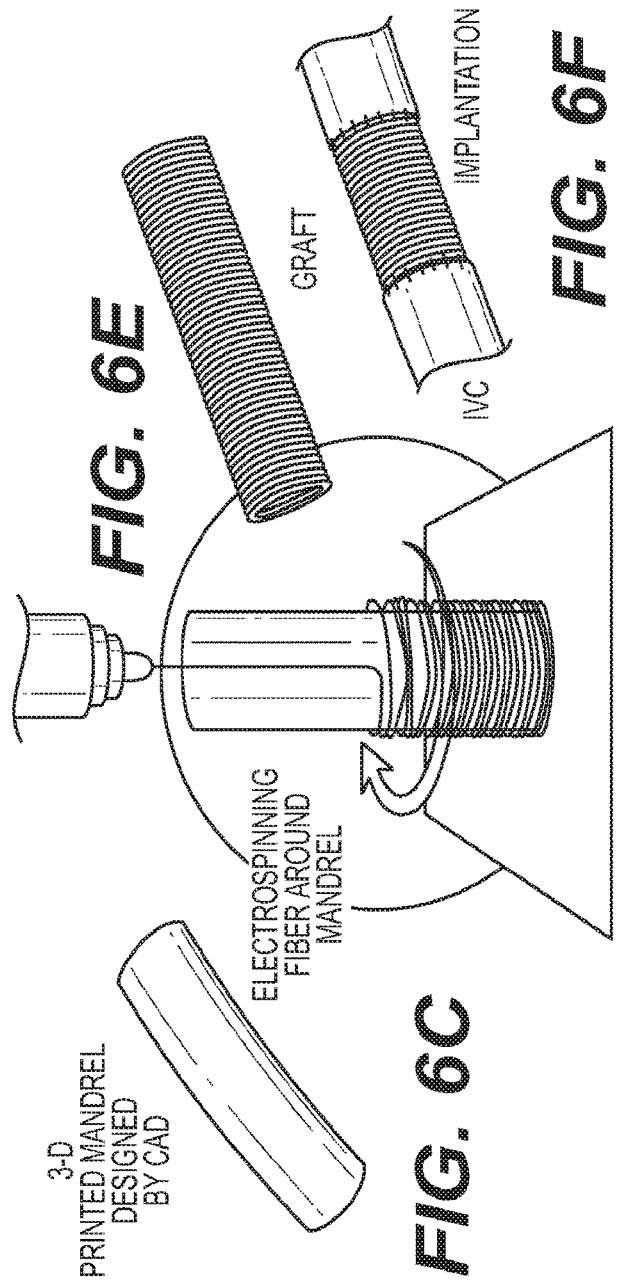

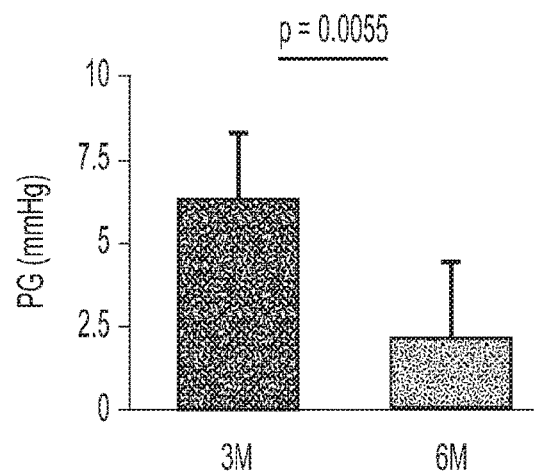
*FIG. 8C*
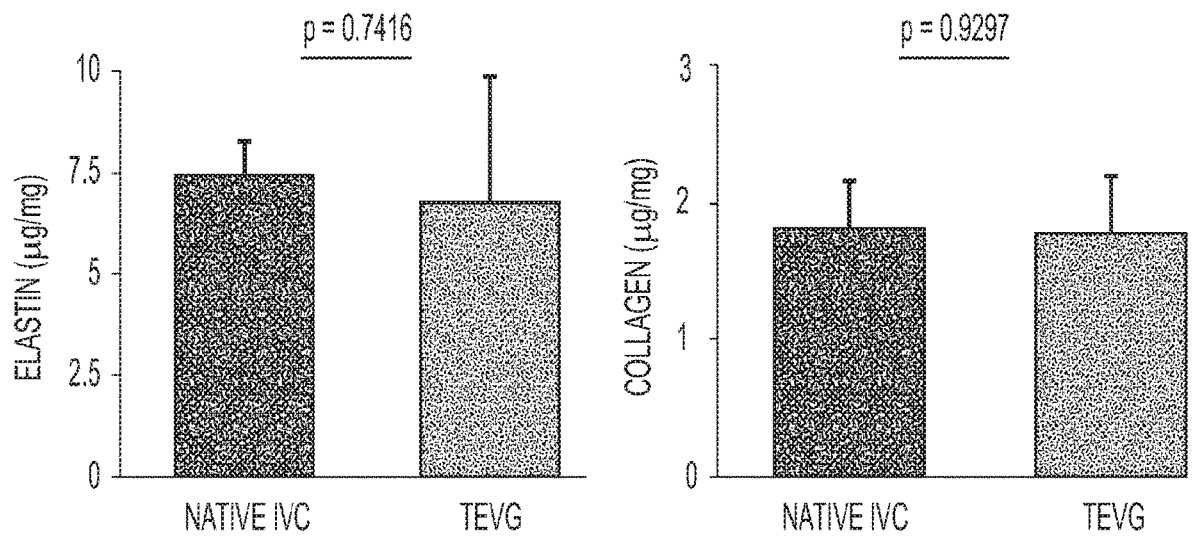
*FIG. 8E*  *FIG. 8D*

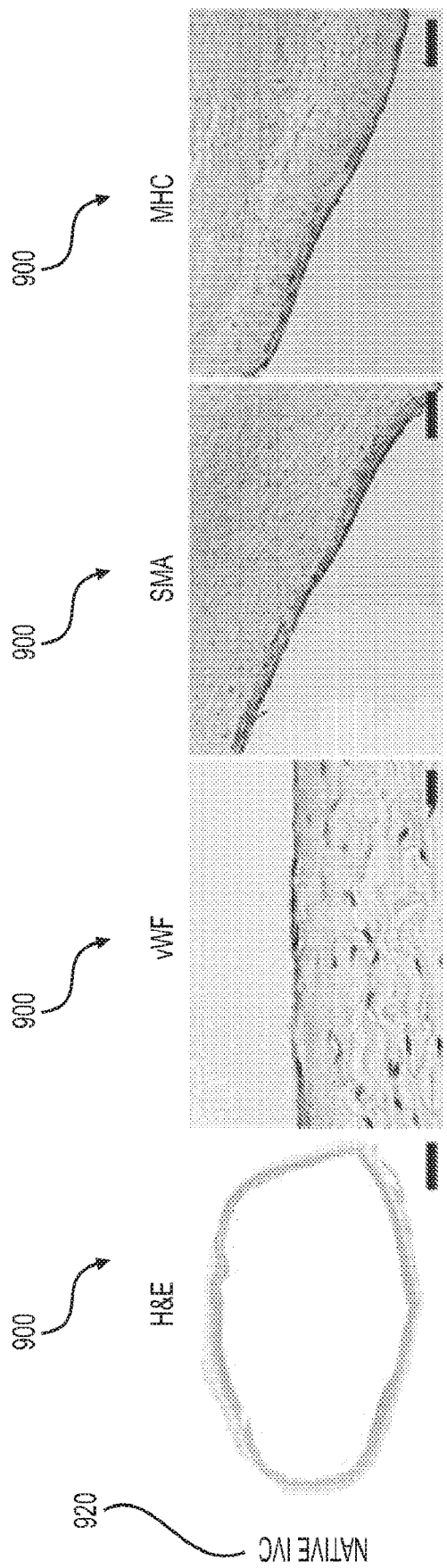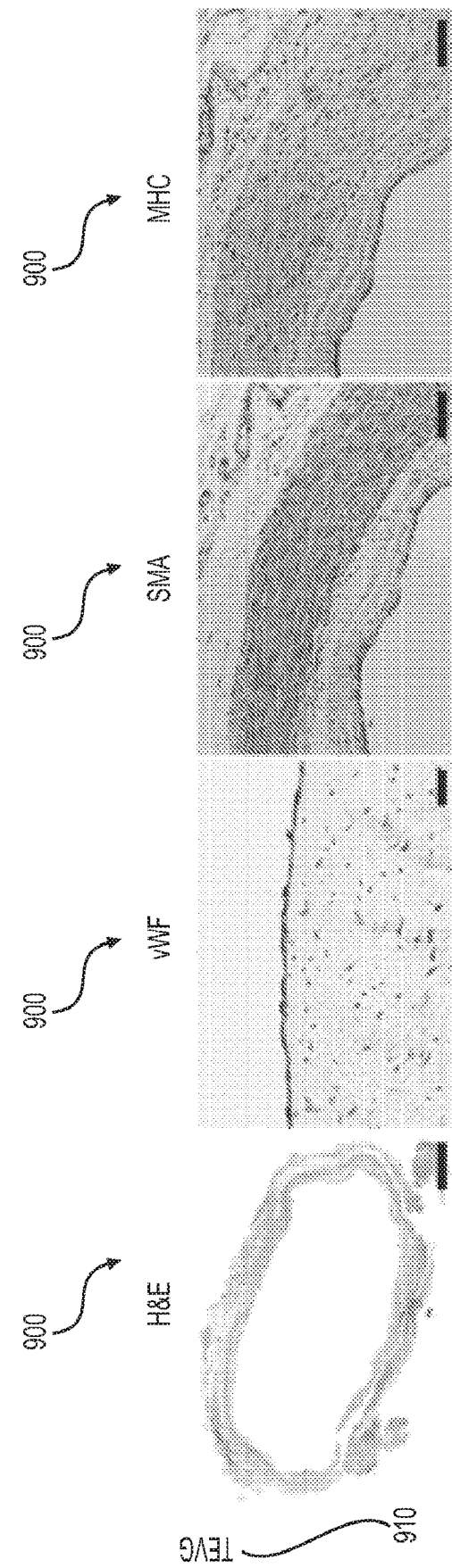

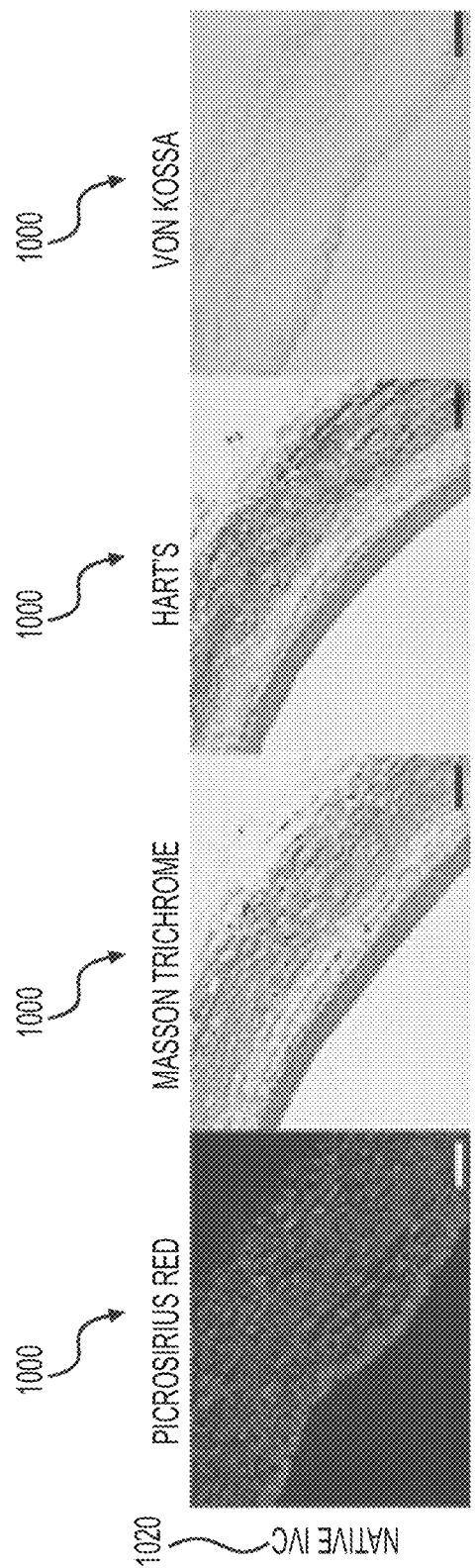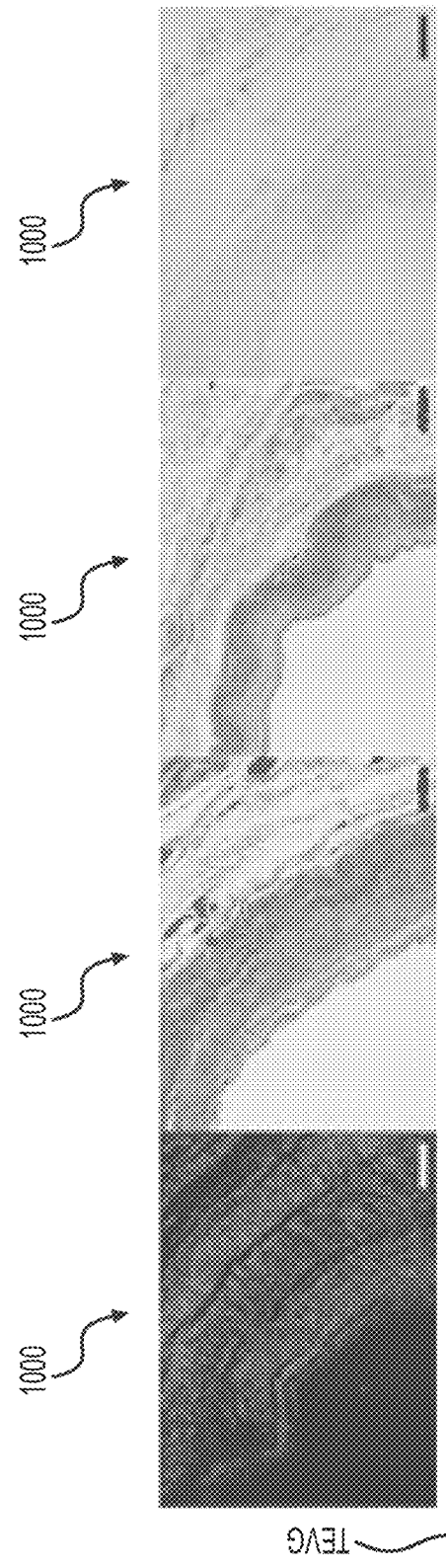

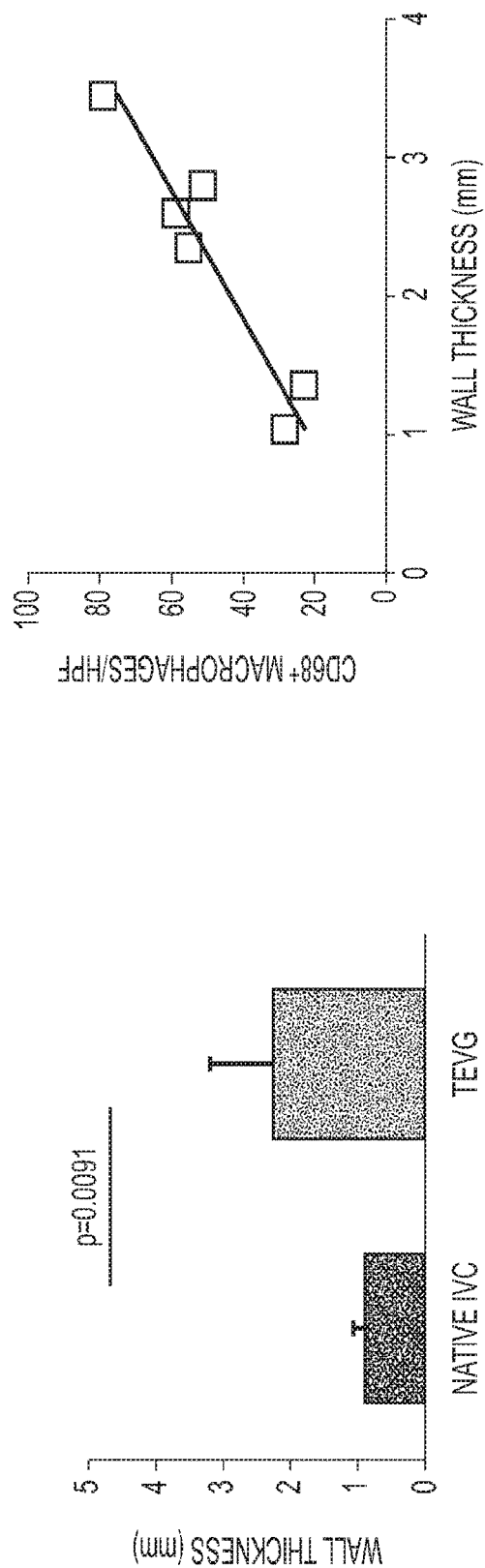
FIG. 11A
FIG. 11B
FIG. 11C

METHOD FOR GENERATING AN ELECTRO SPUN FIBER MEDICAL IMPLANT

CROSS-REFERENCE TO RELATED APPLICATIONS

This application is based upon and claims the benefit of priority to provisional U.S. Application No. 62/209,990, filed Aug. 26, 2015, the entire contents of which are incorporated herein by reference.

BACKGROUND

Field of Disclosure

The present disclosure relates generally to a method of manufacturing patient specific tissue-engineered vascular conduits based on electrospinning. In particular, the present disclosure relates to creating vascular grafts for use in the repair of congenital heart defects, and other vascular abnormalities and diseases.

Description of Related Art

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Congenital heart disease (CHD) is among the leading causes of death associated with congenital anomalies in the newborn period. For instance, in the United States alone, nearly 40,000 infants are affected each year by CHD. Approximately 25% of babies born with CHD each year, require invasive or other potentially lifesaving treatment.

Single ventricle anomalies (SVAs) make up one of the largest groups of CHDs. In untreated SVAs, only one of two ventricles is of functional size and is associated with a 70% mortality rate during the first year of life. In order to treat SVAs, a graft is implanted to connect the inferior vena cava (IVC) and the pulmonary artery. There are a number of other situations in congenital cardiac surgery, where a tube-like connection is established using a conduit. However, the implanted grafts include complications such as progressive obstruction, lack of growth potential, increased susceptibility to infection, and increased risk for thromboembolic complications. Further, biological grafts lack growth potential and have poor durability due to calcification and secondary graft failure (e.g., the grafts have failure rates of 70-100% in 10-15 years), and thus require subsequent replacement.

Tissue engineered vascular grafts (TEVGs) offer a potential strategy for overcoming the complications of commercially available grafts like Dacron and ePTFE (Gore-Tex), by providing a scaffold for the patient's own cells to proliferate and provide physiologic functionality, see e.g., U.S. Pat. Pub. No. 2013/0150963, incorporated herein by reference. However, current TEVG strategies do not address the issue of having diversity in the graft shape of each patient. In other words, the current TVEGs do not address the diverse anatomic requirements of individual patients. Accordingly, surgeons are faced with the problem of having to construct complex vessel shapes using a limited choice of grafts under crucial time constraints during surgery.

Accordingly, there is a requirement of a technique for achieving proper graft orientation and shape, in order to reduce the number of re-operations that occur due to graft failures, and achieve a successful CHD corrective surgery.

SUMMARY

Recent progress in imaging technologies such as ultrasound, computed tomography (CT), and magnetic resonance imaging (MM) provide surgeons detailed, three-dimensional (3D) views of complex cardiac and vascular anatomy of congenital heart disease before surgery. By one embodiment of the present disclosure, the 3D images obtained from patients are modified by a computer model for the purpose of printing a patient-specific mandrel, and subsequent creation of a electro spun fiber vascular graft using electrospinning. Thus, it is envisioned that improved patient care can be obtained by manufacturing patient-specific electro spun fiber vascular grafts. The electro spun fiber vascular grafts promote neo-tissue formation and reduce complications. Such a technique drastically enhances the available treatments available for children suffering from CHD and adults with vascular disease.

Potential uses of the patient-specific electro spun fiber vascular grafts include applications in Fontan conduits/total cavo-pulmonary connection, modified Blalock-Taussig shunts, right ventricle-to-pulmonary artery (RV-PA) conduit, aortic arch reconstruction, interrupted aortic arch repair, co-arctation of the aorta repair, hemodialysis grafts, truncus arteriosus repair, aortic aneurysm repair (ascending thoracic, descending thoracic, thoracoabdominal, abdominal), conduits with valves (including valved RV-PA conduits), patches with valves (as in Tetralogy of Fallot repair), patches for angioplasty, and valves and rings for valvuloplasty (aortic, mitral, tricuspid, pulmonary). Moreover, the patient specific conduits can be developed to assist with vascularization of transplant organs to better suit the anatomy of the patient.

According to one embodiment there is described a method for generating a electro spun fiber medical implant including determining dimensions of a portion of anatomy of a patient corresponding to the electro spun fiber medical implant via medical imaging, generating a model of the portion of the anatomy based on the dimensions, the model including one or more solid areas and one or more void areas encompassed within the one or more solid areas, inverting the model to generate a mandrel model, the mandrel model generated based on the one or more void areas, generating the mandrel based on the mandrel model, the mandrel including at least one electrically conductive material therein, and applying an electrospinning process to the mandrel to generate the electro spun fiber medical implant which circumscribes the mandrel, wherein the mandrel is removable from within the electro spun fiber medical implant after a disassembly process.

According to another embodiment there is described a system for generating a electro spun fiber medical implant. The system includes circuitry configured to determine dimensions of a portion of anatomy of a patient corresponding to the electro spun fiber medical implant via medical imaging, generate a model of the portion of the anatomy based on the dimensions, the model including one or more solid areas and one or more void areas encompassed within the one or more solid areas, invert the model to generate a mandrel model, the mandrel model generated based on the one or more void areas, and transmit the mandrel model to a printing device configured to generate the mandrel based on the mandrel model, the mandrel including at least one electrically conductive material therein.

According to another embodiment there is described a medical implant system including a mandrel and a electro spun fiber medical implant. The mandrel is generated based on a mandrel model, the mandrel including at least one electrically conductive material therein. The mandrel model is generated based on one or more void areas obtained by inverting a model. The model is of a portion of anatomy of a patient and is generated based on dimensions of the portion of anatomy of the patient corresponding to the electro spun fiber medical implant, determined via medical imaging. The model includes one or more solid areas and the one or more void areas encompassed within the one or more solid areas. The electro spun fiber medical implant is generated by applying an electrospinning process to the mandrel to generate the electro spun fiber medical implant which circumscribes the mandrel. The mandrel is removable from within the electro spun fiber medical implant after a disassembly process.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

Various embodiments of this disclosure that are proposed as examples will be described in detail with reference to the following figures, wherein like numerals reference like elements, and wherein:

FIG. 1 illustrates exemplary staged surgical palliations for single ventricle anomalies of congenital heart disease;

FIG. 6 depicts an exemplary schematic workflow illustrating the manufacturing and surgical implantation of a nano-fiber graft in a sheep model;

FIGS. 8A-8E illustrate exemplary results pertaining to quantitative biochemical analysis of the implanted grafts;

FIG. 9 depicts exemplary snapshots illustrating photomicrographs of native IVC and tissue engineered vascular grafts;

FIGS. 11A-11C show exemplary illustrations depicting a comparison of wall thickness between native IVC and tissue engineered vascular grafts;

DETAILED DESCRIPTION OF EMBODIMENTS

Figure 2:
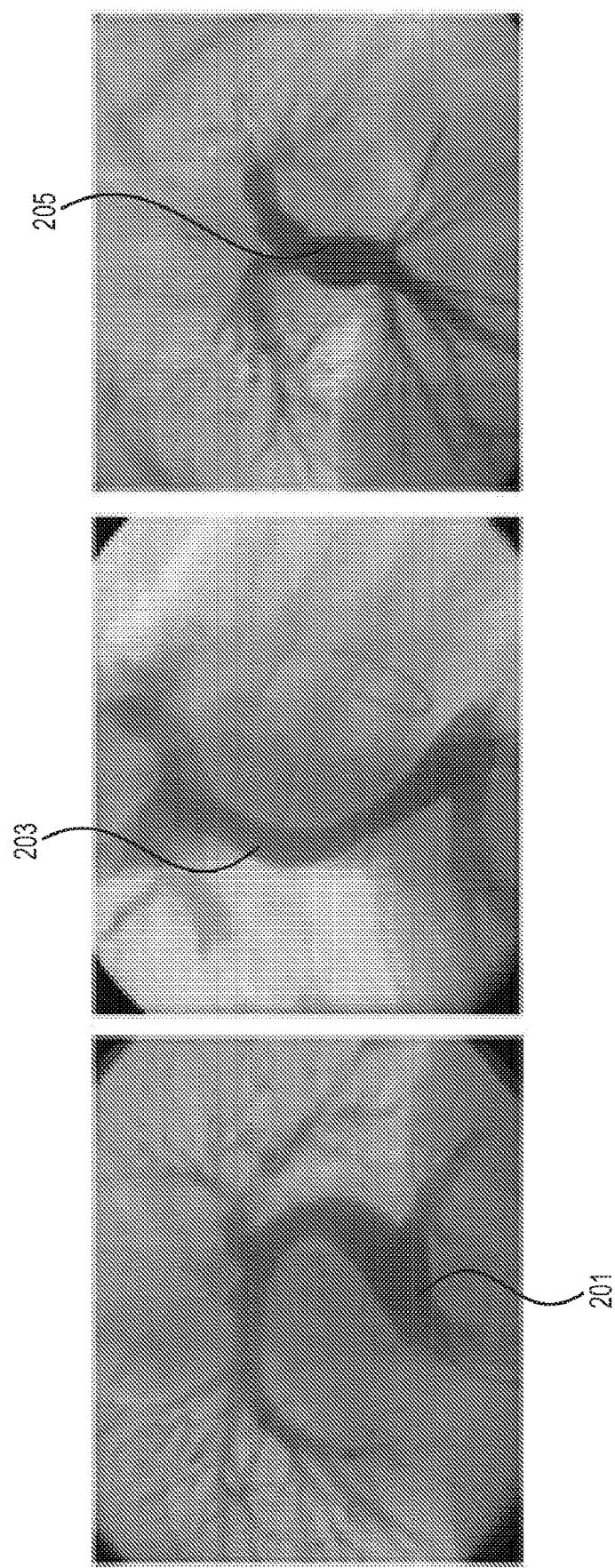
FIG. 2 is an exemplary illustration depicting anatomical variations of Fontan pathway.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as 'an embodiment', 'one embodiment' and 'another embodiment' may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

Embodiments of the present disclosure provide for the generation of a pre-operative patient-specific electro spun fiber vascular graft. The electro spun fiber vascular graft is shaped to match a specific patient's anatomy and is optimized for fluid flow that is computed based on flow dynamic simulations. A electro spun fiber vascular graft as described herein requires minimal modifications during implantation surgery, and thereby makes surgery easier and simpler. Furthermore, the electro spun fiber graft promotes cell adhesion and proliferation, and thereby prevents conduit stenosis (i.e., abnormal narrowing) and maintains good long-term cardiac functioning.

In what follows, is provided a non-limiting example illustrating the requirement and importance of having a patient specific graft design in the treatment of congenital heart disease (CHD).

FIG. 1 illustrates exemplary staged surgical palliations for single ventricle anomalies of congenital heart disease. As stated previously, single-ventricle-anomalies (SVAs) make up one of the largest and most severe groups of CHDs. In untreated SVAs, only one of two ventricles is of functional size and is associated with a 70% mortality rate during the first year of life.

In order to treat SVAs, a three-staged surgery is performed as shown in FIG. 1. The first stage includes establishing stable sources of aortic and pulmonary blood flow using a shunt. Specifically, a modified BT-shunt is created to channel aortic flow to the pulmonary arteries (PAs). This procedure is typically performed in the first week of life. In the second stage (referred to as the bidirectional Glenn procedure), the superior vena cava (SVC) is disconnected from the heart and re-implanted into the PAs at about 4-6 months of age. In the third and final stage (also referred to as the Fontan procedure), the inferior vena cava (IVC) is connected to the PAs via a lateral tunnel (LT) or an extra-cardiac (EC) Gore-Tex tube, approximately 2-4 years after the first stage.

The Fontan pathway, as shown in Stage 3 of FIG. 1 is highly variable in each patient. FIG. 2 depicts an exemplary illustration of the anatomical variations of Fontan pathway. Specifically, FIG. 2 depicts three unique anatomical variations of Fontan pathway (201, 203, and 205, respectively), for three different patients via angiography after a Fontan operation. The Fontan pathway is seldomly straight and has many variances. For such different anatomies, surgeons routinely need to construct optimal shapes during surgery to fulfill their needs. Such variations in architecture demonstrate the requirement for customizing a graft prior to implantation, in order to accommodate proper blood flow and connection between the IVC and pulmonary artery.

Figure 3:
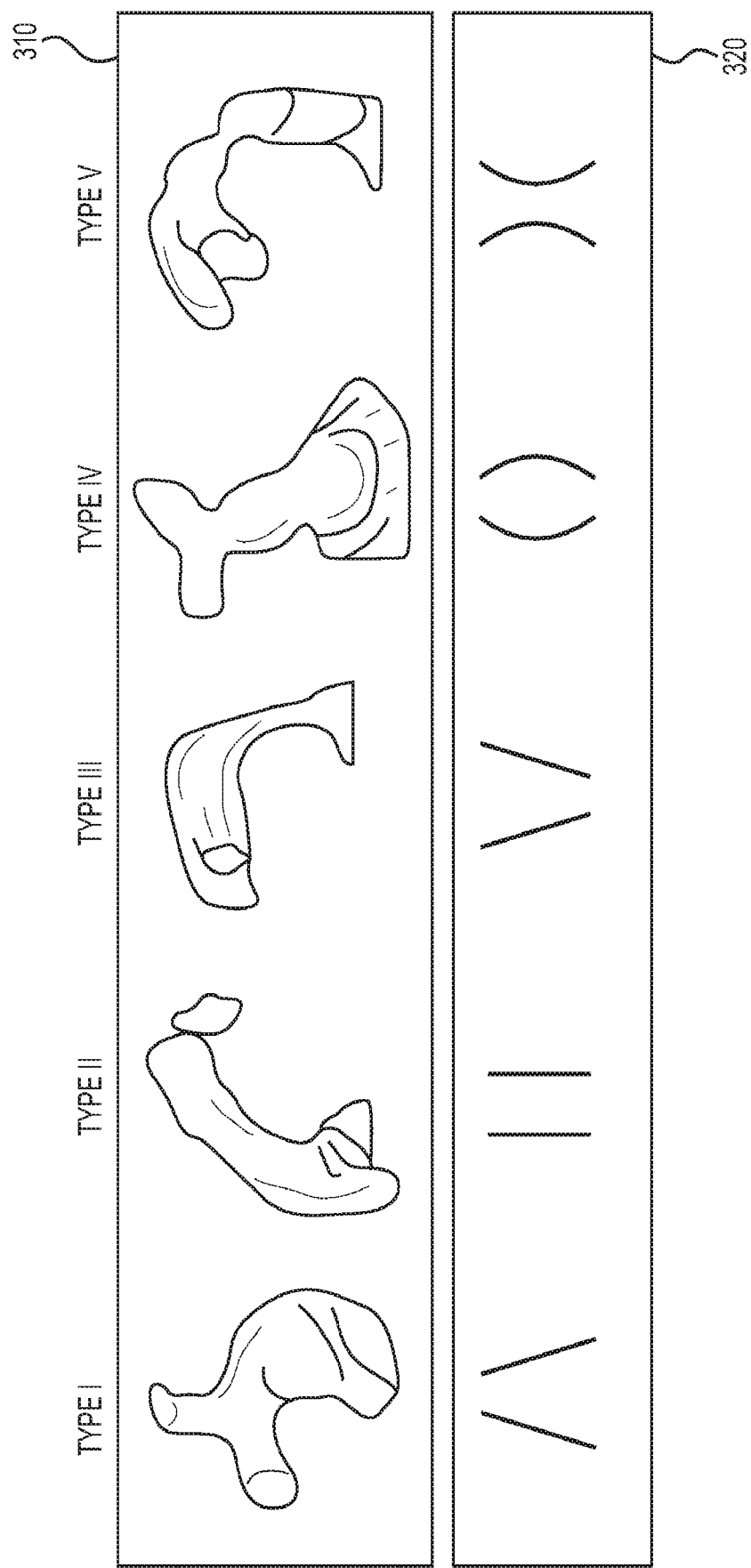
FIG. 3 depicts an exemplary illustration showing variances in anatomies of right-ventricular-pulmonary artery (RV-PA) routes.

Turning to FIG. 3, there is depicted an exemplary illustration showing variances in anatomies of right-ventricular-pulmonary artery (RV-PA) routes. As shown in FIG. 3, three-dimensional ("3D") models of Fontan conduits from different patients (top row, 310), and the hepatic flow distribution between the right pulmonary artery (RPA) and left pulmonary artery (LPA) (bottom row, 320), demonstrate the clinically significant variability in outcome performance for the patient, and that commercially available conduits do not fit well for all patients. Since the blood in the Fontan circulation is passively pumped to the lung by the pressure difference between the vena cava and the left atrium, a small increase of venous resistance in Fontan pathway results in a significant drop in the cardiac output for a modified circulation bypassing the right ventricle, which could cause long-term complications.

There is a strong link between the specific characteristics of blood flow through the Fontan route and the cause or exacerbation of the complication. The most prominent example of such a relationship is the development of pulmonary arteriovenous malformations (PAVM) (causing progressive hypoxia) because of the maldistribution of hepatic factors produced by the liver to the pulmonary vasculature. Another example is the case of impaired exercise capacity, due in part to the non-linear increase in the energy dissipated through the Fontan pathway with increased cardiac output. Accordingly, ensuring an efficient Fontan pathway design with a balanced hepatic flow distribution (HFD) yields long-term benefits for patient health and quality of life.

Furthermore, conduit selection for right ventricular outflow tract (RVOT) and pulmonary artery reconstruction presents a major challenge in the treatment of many CHDs. This is due to the fact that the angle, length, and diameter of RV-PA route varies widely even amongst those individuals with normal cardiac anatomy. In patients with congenital heart disease, such variety is much more pronounced. Moreover, there is no ideal commercially available material for reconstruction of the route from the RV to PA without compromising laminar flow in the graft.

Despite the above stated complexities in surgery for the diverse anatomies, the surgeons have no information of flow-dynamics and hemodynamics data of the reconstructed route during procedure, as the surgical field is required to be bloodless. Thus, surgeons usually design the pathway, based on prior experiences in a limited amount of operation time. Surgeons can obtain the hemodynamics data of the constructed pathway only after the surgery is complete. If there are significant hemodynamic issues, surgeons could perform reconstruction again. However, minor energy loss or unbalanced flow cannot be identified immediately in operating room. Therefore, ensuring a patient-specific graft design for ideal reconstructed route before surgery with a balanced flow distribution and minimum energy loss may yield a long-term benefit for the patient's health and quality of life.

By one embodiment of the present disclosure, is provided a technique of creating patient-specific tissue engineered vascular grafts (TEVGs) for reconstruction in congenital heart disease. The TEVG include biodegradable scaffolds on which autologous cells proliferate and provide physiologic functionality. Specifically, the patient-specific TVEGs are created based on 3D-printing and electrospinning technology.

Imaging technologies such as computed tomography (CT) and magnetic resonance imaging (MRI) provide surgeons detailed, three-dimensional (3D) views of complex cardiovascular anatomies before surgery. Such technologies offer significantly more utility since the advent of 3D-printing technology, and greatly enhance available treatment options for CHD patients with complex anatomical or physiological requirements that are not easily addressed using currently available prostheses. Moreover 3D models of Fontan conduits provision for the analysis of hepatic flow distribution between the right and left pulmonary arteries. As described next with reference to FIG. 4, a method of creating a patient-specific TEVG utilizes pre-operative 3D imaging data to 3D-print a customized mandrel upon which a polyglycolic acid (PGA)/poly (L-lactide-co-ε-caprolactone) i.e., PLCL electro spun fiber blend is electrospun.

Figure 4:
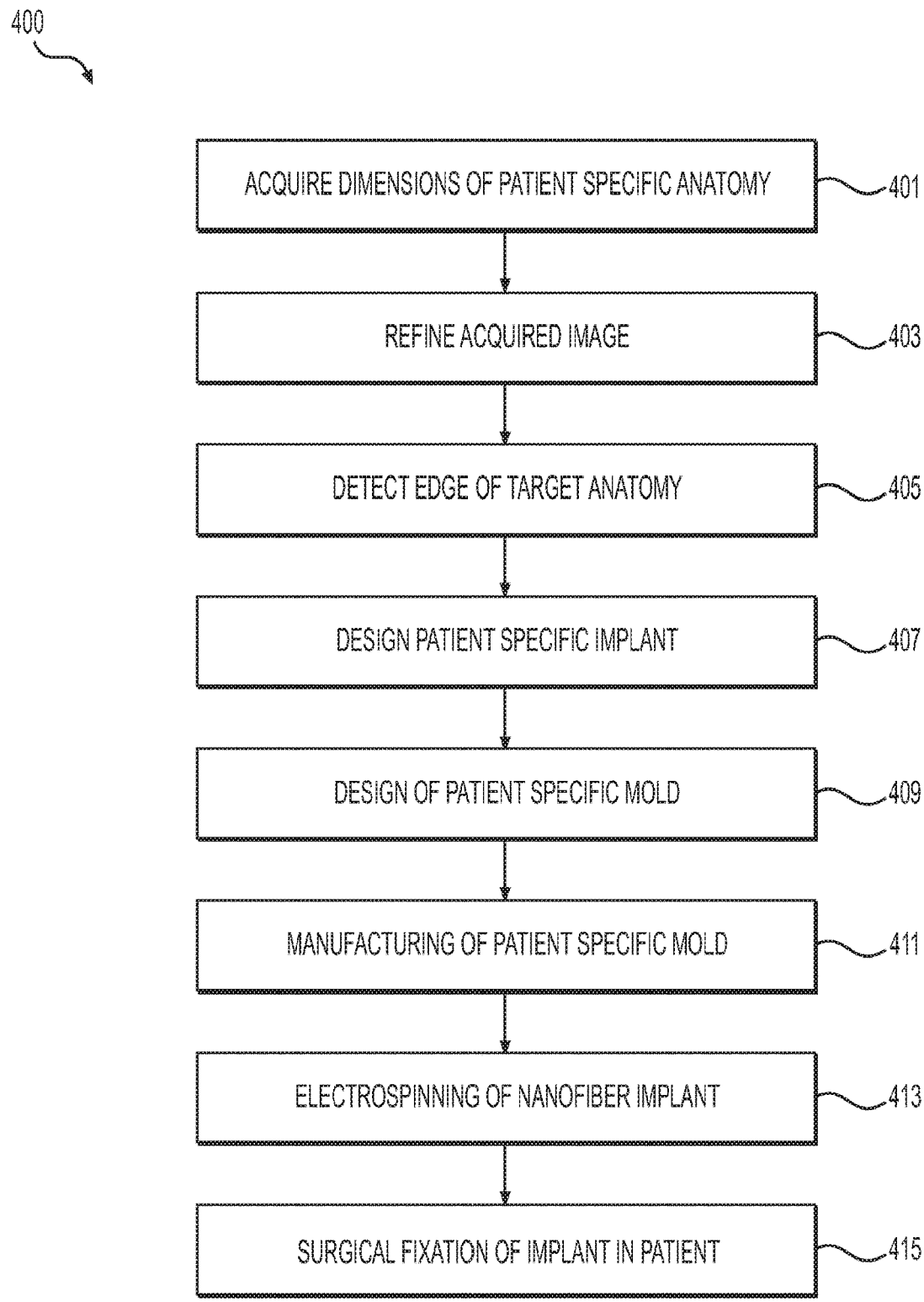
FIG. 4 depicts a flowchart outlining the steps performed in designing and manufacturing a patient-specific vascular graft.

FIG. 4 depicts a flowchart 400 outlining the steps performed in designing and manufacturing a patient-specific vascular graft.

The process commences in step 401 wherein geometry of the patient's anatomy is determined by acquiring 3D images of target tissue using plenoptic, stereo, time of flight, or structured light cameras, or clinical imaging techniques. Specifically, imaging techniques such as CT, MM (described later with reference to FIG. 14), 3D-ultrasound, PET-CT, laser and the like may be utilized to obtain images of the patient's anatomy.

In step 403, signal processing is performed on the acquired images in order to refine the images. Various signal processing operations such as low pass filtering, high pass filtering, Gaussian filtering, de-noising, smoothing, sharpness, and contrast operations and the like may be performed to enhance the tissue edges in the acquired images.

In step 405, the process implements edge detection algorithms in order to detect the edges of target tissue and distinguish them from surrounding tissues.

The process further proceeds to step 407, wherein a patient-specific implant is designed. Specifically, using dimension, vector, or freeform software (e.g., computer-aided-drafting (CAD)), a patient specific implant (model) is designed from measurements acquired from target anatomy.

By one embodiment, the implant may be designed to match existing geometry, or optimized per procedure i.e., increasing flow rates or maximizing functional output requirements. For instance, one or more flow simulations could be applied to the generated patient specific implant model. The model could then be adjusted based on the applied one or more flow simulations to enhance flow in the generated patient specific implant model. Furthermore, it must be appreciated that superficial or surface features may be included while determining the design of the patient-specific implant.

In step 409, a patient-specific mold (or model) is designed. By one embodiment, a patient specific mold may be designed by computing the negative of the patient specific implant model, where the negative represents a fill within the void areas within the patient specific implant. In other words, the patient specific implant includes one or more solid areas and one or more void areas encompassed within the one or more solid areas. The void areas are the negative of the solid areas. By one embodiment, the mold may include one or more pieces or halves, or may be a mandrel.

Further, in step 411, the designed patient-specific mold is manufactured to include an electrical conductive layer. By one embodiment, the mold may be realized using additive manufacturing process or by additive manufacturing process with post processing to make the mold electrically conductive.

Upon manufacturing the mold, the process deposits nano-fibers on the mold (i.e., a mandrel) via electrospinning process (step 413). The electrospinning includes depositing nano-fibers on the mold to create the vascular implant, whereafter the mold is removed prior to surgery. It must be noted that electrospinning provides the advantageous ability of being a highly tunable process by which a wide variety of polymer types and fiber sizes can be spun into various shape of mandrels, thus allowing for the rational design of custom made scaffolds for tissue engineering.

In step 415, the implant can be sterilized and surgically fixated in the patient. For instance, the implant may be delivered using catheter based tools, or fixated through surgical intervention to the target tissue in a patient. It must be appreciated that the implant may support, enhance, or replace target tissue in the patient.

Accordingly, the 'patient-specific' vascular graft, which is manufactured by the process as described above, is sized and shaped for surgery for the specific patient, thus expediting the corrective surgical procedure. Moreover, the vascular graft improves the quality and safety of vascular graft implantations, and is able to maintain optimal flow through vasculature reconstruction, and recapitulates the native mechanical properties.

By one embodiment, as stated above, based on pre-operative angiography images, the diameter and length of the patient's IVC can be measured and matching graft models can be designed using CAD software. The final mandrel design can be converted to a stereo-lithography (STL) format and exported for 3D fabrication out of material such as stainless steel-420.

According to one embodiment, the mandrel may be manufactured using additive manufacturing techniques. The mandrel may be made from solid metals (including titanium, steel, stainless, aluminum, brass, bronze, gold); of hollow metal structures with a thin section to break away the mandrel before surgery; of liquefiable metals e.g. through heating that allow easy removal of mandrel; of polymers with conducting coating, plating or paint (silver, chrome, gold, etc); of liquefiable polymers with conductive coating, plating or paint; of hollow polymer structures with thin section to break away mandrel with conducting coating, plating or paint; and of conductive polymers (e.g. resin contains conductive elements). Additionally, metal and coated polymer mandrels may also be manufactured by subtractive methods such as cutting, turning, etc. The manufactured mandrel can be matched with the patient's anatomy or can be shaped to create an implant that optimizes functional outcomes such as burst pressure, compliance, and the like (described below) for the patient.

By one embodiment, the mandrel may be manufactured to have a smooth finish for easy removal of the electrospun implant from the mandrel. Additionally, the mandrel may undergo post processing in order to polish, buff, smooth, apply a non-stick coating, and reduce surface friction, such that the implant can be easily removed from the mandrel after electrospinning. The mandrel can be coated with an electrically conductive substance such as a coating of electroplating nickel, copper, or other metal. Alternatively, the coating can also be a conductive paint, conductive glue or epoxy.

Furthermore, by one embodiment, the mandrel can be manufactured by an additive manufacturing process using a non-electrically conductive material. The non-conductive material can be mixed with a conductive material at the time of manufacturing in order to generate an electrically conductive mandrel. For instance, the mandrel may be a mixture of non-conductive material and aluminum shavings, wherein the aluminum shavings compose a substantially large concentration in order to make the mandrel electrically conductive.

Additionally, by one embodiment and as stated previously, a subtractive manufacturing process can be used to create a mold that is the negative of the mandrel. A conductive material (e.g., stainless steel) can be cast in the mold and used as the mandrel. Furthermore, a liquefiable metal or polymer can be cast in the mold to take the shape of the mandrel. After electrospinning, the mandrel can be liquefied by application of heat or other medium such as warm water to liquefy the mandrel for removal from the electrospun implant.

According to one embodiment, the mandrel may be manufactured from a plurality of pieces that can be snapped together or taken apart to create more complex geometry. The use of several pieces also enables easy removal of the mandrel after electrospinning. The mandrels can also include a lock and key feature that allows portions (i.e., pieces) of the mandrel to be aligned and be snapped together. Furthermore, the mandrels may be thin walled, or include thin walled portions that facilitate the breaking of the mandrel into smaller mandrels in order to facilitate easy removal of the mandrel from the electrospun implant. Additionally, by one embodiment, the mandrels may be hollow with thin walls and perforations, so that bifurcated mandrels can be manufactured. The perforations also enable easy removal of the individual portions of the mandrel upon electrospinning.

By one embodiment, the manufactured mandrels may include one or more conductive and non-conductive portions. The conductive portions of the mandrel may include more than one conductive material. In this manner, by varying the location of the conductive portions of the mandrel, one can generate a conductivity gradient across the mandrel. Such a feature provides the advantageous ability of depositing electro spun fiberin a concentrated fashion in different areas of the graft via electrospinning.

For the treatment of CHD, in addition to the complexity of surgery for the diverse anatomies, another significant source of morbidity and mortality arises from the use of synthetic biomaterials for various reconstructive cardiac operations. These materials do not grow and cause calcification, which require the patients multiple surgeries in the long term. Accordingly, by one embodiment of the present disclosure, FDA approved biodegradable materials are used in the manufacturing the vascular scaffold. The biodegradable materials offer a potential strategy for overcoming calcification complications by providing a biodegradable scaffold for the patient's own cells to proliferate and provide physiologic functionality over time.

Despite the strong potential of 3D printing to improve regenerative strategies, there are many challenges that relate to the biomaterials that are available for printing. Materials used for 3D bio-printing must adhere to three key characteristics: the scaffold materials should be a) biocompatible, b) support cell growth and differentiation, and c) be able to sufficiently retain their shape in order to preserve scaffold integrity until solidification locks in the scaffold geometry. Thus, by one embodiment, the scaffolds can be made from materials such as polyglycolide (PGA) and polylactide-co-caprolactone (PLCL)) in a electro spun fiber form. Other materials may include PDO (polydioxanone), PCL (polycaprolactone), PLGA (poly lactic-co-glycolic acid), polyurethane (PU), polyethylene terephthalate (PET) or any combination of these materials.

To reiterate, the above described patient-specific vascular grafts are created by utilizing pre-operative 3D imaging, followed by design of a vascular graft using computer aided design (CAD) model, 3D printing of a mandrel, and electrospinning of the electro spun fiber vascular grafts. The patient is imaged using a 3D medical imaging technique such as MRI, whereafter the images are processed and segmented to reveal the relevant anatomy. A graft is further designed using for instance, CAD software to optimally (both with respect to anatomical fit and optimal flow characteristics) fix the defect. Further, an electrically conductive mandrel is created from the CAD model of the graft, e.g. using 3D metal printing techniques. A polymer solution is electrospun to deposit electro spun fiberonto the conductive mandrel. According to one embodiment, by changing electrospinning parameters such as fiber material, fiber size, fiber thickness, voltage, spin speed, spin duration, the created grafts are manufactured to match the material properties (e.g. compliance) of the native vessels and promote neo-tissue formation (e.g. through porosity). The graft is then removed from the mandrel, sterilized, and implanted into the patient.

In what follows, is provided a detailed description of an experimental evaluation of the above method of manufacturing the patient-specific graft. Specifically, an electrospinning mandrel is 3D-printed after computer-aided design based on preoperative imaging of the ovine thoracic inferior vena cava. TEVG scaffolds are then electrospun around the 3D-printed mandrel. Six patient-specific TEVGs are implanted as cell-free inferior vena cava (IVC) interposition conduits in a sheep model, and were explanted after 6 months for histologic, biochemical, and biomechanical evaluation. The experiments as described below confirm the feasibility of utilizing a patient-specific electro spun fiber TEVG by evaluating neo-tissue formation, biocompatibility, and mechanical properties after the 6-month implantation period in the sheep model.

Figure 5:
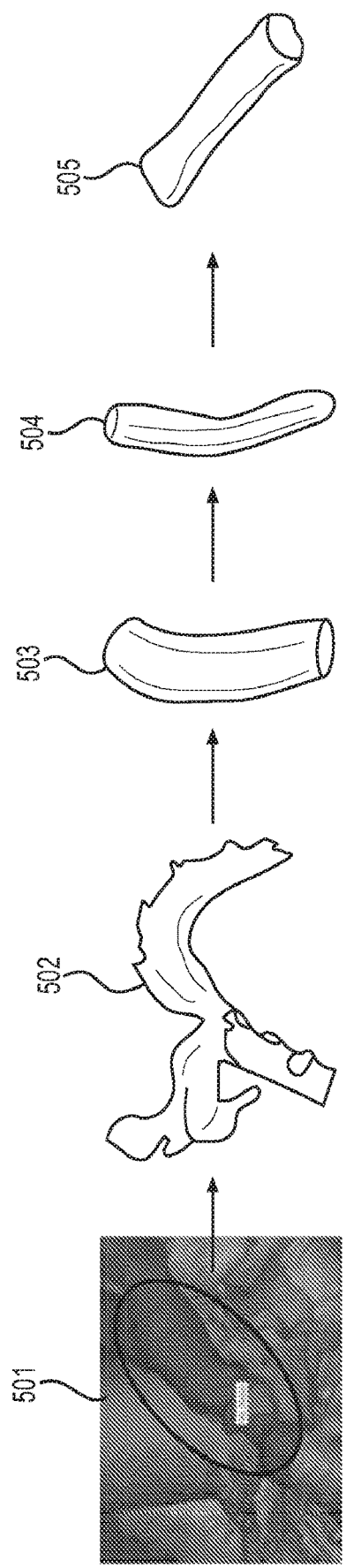
FIG. 5 depicts an exemplary schematic flow chart illustrating the process of manufacturing patient-specific tissue engineered vascular grafts.

The experiment utilizes pre-operative 3D imaging data to 3D-print a customized mandrel upon which a PGA/PLCL electro spun fiber blend is electrospun, yielding a patient specific TEVG as shown in FIG. 5.

FIG. 5 depicts an exemplary flow chart illustrating the process of manufacturing patient-specific tissue engineered vascular grafts. As shown in FIG. 5, the 3D image of vasculature is segmented (step 501) to create a patient specific graft design from the preoperative CT image using computer aided design system (step 502). Further, a finalized mandrel (step 503) is 3D printed from stainless steel (step 504). The patient-specific electro spun fiber graft (as shown in step 505) is obtained via electrospinning and removal of the mandrel.

According to one embodiment, based on preoperative angiography images, the diameter and length of the sheep IVC are measured and matching graft models are designed using CAD software. The final mandrel design is converted to STL format and exported for 3D fabrication which is performed using materials such as stainless steel. Furthermore, the mandrel manufactured by the additive manufacturing process provides the advantageous ability of having a quick turn-around time. Specifically, the mandrel manufactured by the additive manufacturing process can be used to create patient-specific grafts within a week or less of the surgery. Additionally by one embodiment of the present disclosure, the mandrel may be made of a liquefiable material, thereby allowing the release of the mandrel from the electro spun graft in an easy fashion. Furthermore, the use of liquefiable mandrels also provisions for forming complex shapes of the graft.

FIG. 6 depicts an exemplary schematic workflow illustrating the manufacturing and surgical implantation of a nano-fiber graft for sheep. As shown in FIG. 6, the dimension and shape of the thoracic inferior vena cava (IVC) is measured from angiography prior to surgery in sheep model (step A, and step B). In step C, an electrospinning mandrel is modeled by computer aided design and subsequently 3D-printed. Thereafter, in step D, a nano-fiber scaffold is electrospun onto the 3D printed mandrel. A patient-specific cell-free electro spun fiber TEVG is implanted as IVC interposition conduit in the sheep model (steps E and F). Steps G and H in FIG. 6, depict a scanning electron microscope (SEM) image of the scaffold at a magnification scale of 500× and 4000×, respectively. For sake of completeness, step I depicts an intraoperative picture of the implanted graft in the sheep.

According to an embodiment, in order to create the co-electrospun polyglycolic acid (PGA) and polylactide-co-caprolactone (PLCL) scaffolds, 10 wt % PGA is dissolved in hexafluoroisopropanol (HFIP) and 5 wt % PLCL is dissolved in HFIP. Each solution is stirred via a magnetic stir bar for at least 3 hours at room temperature. In separate syringes, the PGA solution is dispensed at a flow rate of 2.5 mL/hr and the PLCL solution is dispensed at a flow rate of 5.0 mL/hr to create a graft with a 1:1 PGA: PLCL ratio. Both solutions are simultaneously electrospun onto the custom 3D-printed mandrel that was positioned 20 cm from the needle tip and rotated at 30 RPM. A +25 kV charge is applied to each syringe tip and electrospun electro spun fiberare deposited onto the grounded mandrel until the desired wall thickness was achieved. Eventually, the electrospun scaffold is removed from the mandrel, and terminally sterilized.

Upon implantation of the scaffold within the test subject (sheep), a plurality of analysis and testing is performed to qualitatively determine the performance of the scaffold. By one embodiment, the plurality of conducted tests include at least a mechanical testing process that determines compliance and burst pressure of the scaffold, a histological and quantitative analysis, and a biochemical analysis.

By one embodiment, six custom made cell-free electro spun fiber TEVGs are implanted as IVC interposition grafts in sheep whose body weights are in the range of 23.9±5.0 kg. The IVC is exposed and heparin (100 IU/kg) is administered intravenously. The TEVG is implanted as an IVC interposition graft using standard running 6-0 prolene suture. Further, angiography is performed to assess any potential graft complications at the 3- and 6-month time points. A catheter is inserted into the jugular vein to the IVC, and intravenous contrast manually-injected into the IVC and mid-graft. Additionally, the IVC blood pressure is measured at the proximal and distal anastomoses to evaluate the pressure gradients (PG) across the graft.

According to one embodiment, compliance and burst pressure data is acquired using a universal mechanical testing machine Specifically, data is acquired using a load frame fitted with a 50 lb. load cell with a force resolution of $10^{-4}$ pounds, and a linear displacement resolution of $10^{-8}$ inches. Compliance testing is performed using a displacement velocity of 1.5 mm per minute, and acquisition rate of 4 data points per second utilizing Laplace's Law to correlate linear force and displacement to compliance.

In a similar manner, burst pressure testing is performed using a displacement velocity of 50 mm per minute and acquisition rate of 4 data points/sec utilizing Laplace's Law to correlate linear force and displacement to burst pressure. By one embodiment, ring samples are placed around two parallel L-shaped steel rods, wherein one rod is attached to the base of the testing machine and the other to the load cell. The samples are strained perpendicular to the length of the sample. Compliance is calculated using systolic and diastolic pressures of 120 mmHg and 80 mmHg, respectively, and burst pressure is calculated as the maximum pressure immediately preceding failure.

According to one embodiment, elastin content is determined using a Fastin colorimetric assay. 100 mg dry weight of each sample is measured and transferred to 1.5 ml micro-centrifuge tubes containing 750 μl 0.25 M oxalic acid. The tubes are further placed on a heat block for 60 min at 100° C. to convert insoluble elastin to water-soluble a-elastin. The elastin content in each sample is determined by detection at 513 nm and interpolation to a standard curve after precipitation and dye binding following the manufacturer's protocol.

Additionally, by one embodiment, collagen content is determined by a Sircol colorimetric assay. 100 mg dry weight of each sample is measured and transferred to low protein binding 1.5 ml conical micro-centrifuge tubes containing 1.0 ml of pepsin (Sigma-Aldrich), with a concentration of 0.1 mg/ml of 0.5 M acetic acid to solubilize the collagen by means of overnight incubation. The collagen content in each sample is determined by detection at 555 nm and interpolation to a standard curve after precipitation and dye binding following the manufacturer's protocol.

For all experiments, data is represented as mean± standard error of mean (SEM). The parameter SEM quantifies how precisely one knows the true mean of the population. SEM takes into account both the value of the standard deviation and the sample size. Further, statistically significant differences between groups are determined using Student's t-test and Pearson correlation test. A paired t-test is performed comparing native tissue to tissue-engineered samples, wherein a value of p<0.05 is considered as the two samples being statistically significant.

In what follows is described with reference to FIGS. 7A-7B to FIG. 13, the results of evaluating the tissue engineered samples as compared to native tissue.

By one embodiment, a tubular scaffold created via the previously described electrospinning technique has a uniform wall thickness of 657 μm±36 μm, which is significantly less than the native IVC wall thickness of 1365±476 μm. The scanning electron microscope (SEM) images of the scaffold are shown in FIG. 6.

Figure 7A:
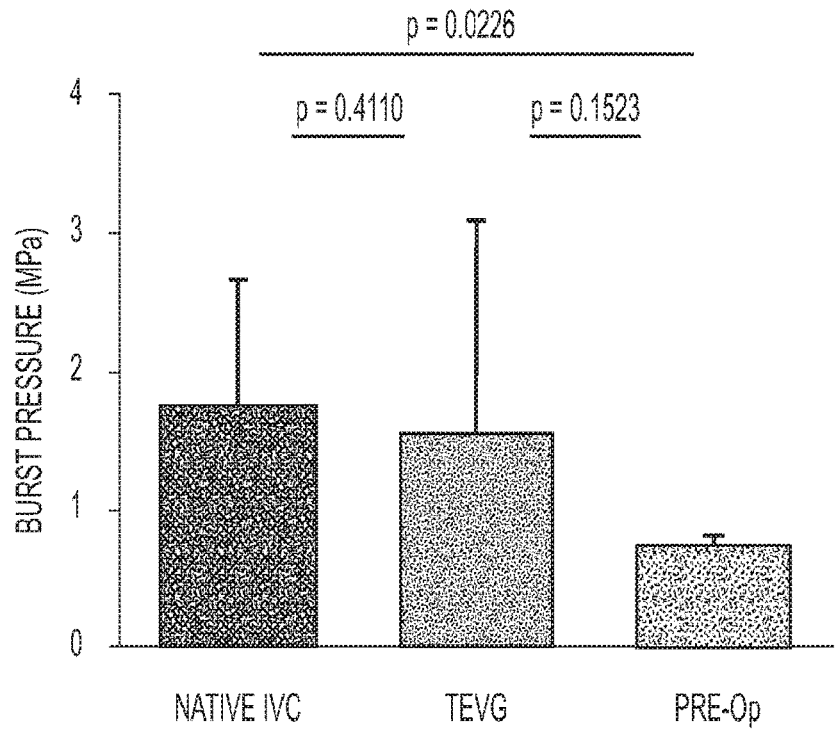
FIG. 7A depicts an exemplary graph illustrating burst pressure of the graft before implantation.

FIG. 7A depicts a graph illustrating burst pressure of the graft before implantation. The burst pressure of the graft before implantation is significantly less than that of the native IVC case. However, it is noted that there is no significant difference in burst pressure between the native IVC and TEVG at 6 months (i.e., a value of 1.74±0.91 MPa, as compared to a value of 1.56±1.53 MPa, for p=0.4110).

Figure 7B:
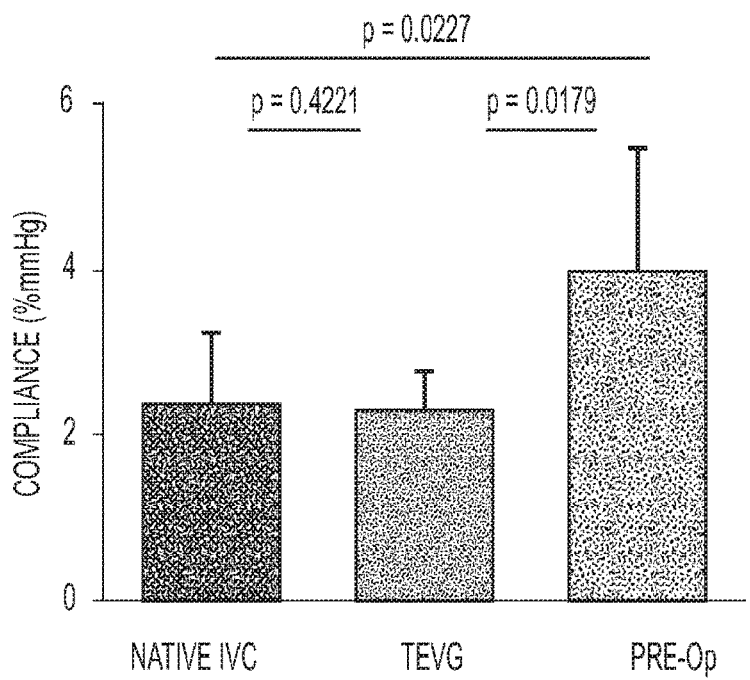
FIG. 7B depicts an exemplary graph illustrating graft compliance.

The pre-operative graft compliance is significantly higher when compared to the native IVC case as shown in FIG. 7B. However, there is no significant difference in compliance between a native IVC and TEVG after 6 months (i.e., a value of 2.37±0.85% as compared to a value of 2.29±0.46%, for p=0.4221).

Figure 8A:
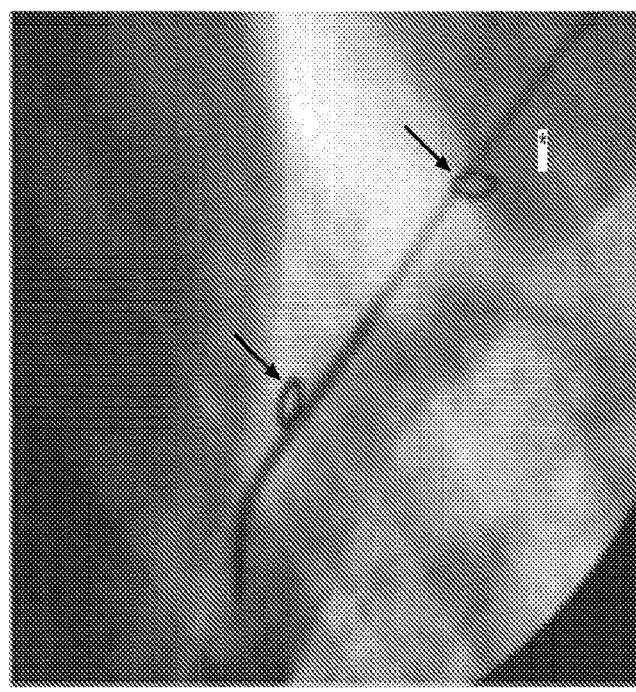

FIGS. 8A-8E illustrate exemplary results pertaining to quantitative biochemical analysis of the implanted grafts. Graft biocompatibility including patency (i.e., a condition of showing detectable parasite infection) and tissue remodeling is observed to be excellent within the 6-month study duration. Furthermore, all sheep survived until the study end point without any graft-related complications, such as stenosis, dilation, or rupture as shown in FIG. 8A. In FIG. 8A, the '*' indicates the right atrium, and the arrows corresponds to the anastomosis site of graft.

Figure 8B:
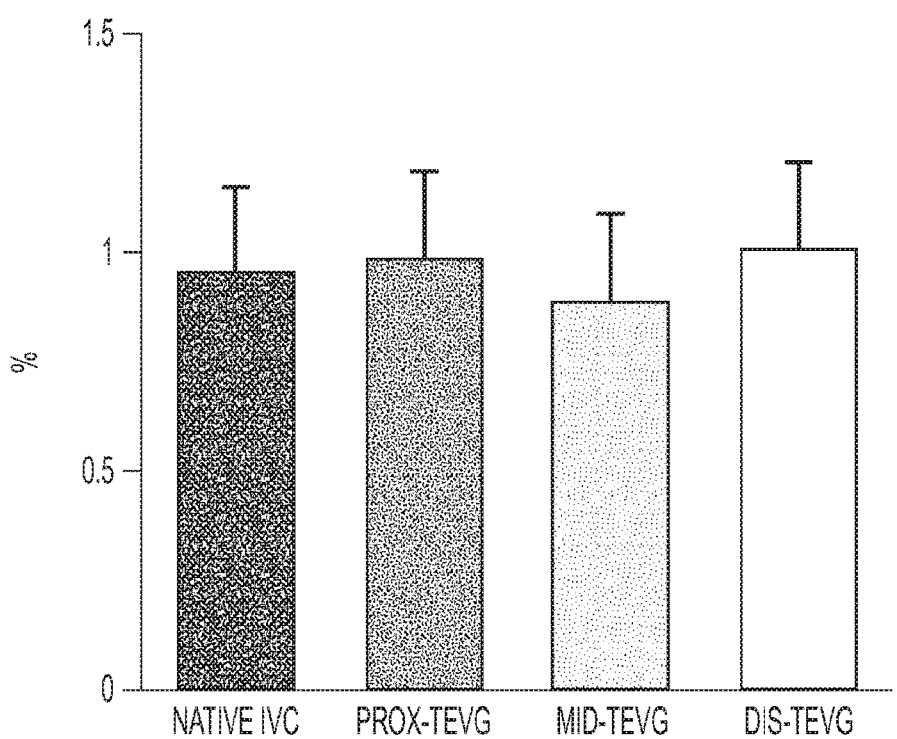

Further, native IVC and the patient-specific TEVG are evaluated at 3 months and 6 months to determine evidence of stenosis or dilation with contrast enhanced angiography. As shown in FIG. 8B, both the IVC and patient-specific TEVG displayed no significant diameter changes between the 3- and 6-month time points.

As shown in FIG. 8C, the pressure gradient (PG) across the TEVG at 6 months is observed to be significantly less than that at 3 months, suggesting advantageous remodeling and scaffold degradation (i.e., a value at 3 months of: 6.29±1.97 vs. a value at 6 months of: 2.08±2.15 mmHg, for p=0.0055).

According to one embodiment, elastin and collagen are important parameters for venous function and are well-studied markers of vascular graft remodeling. Referring to FIGS. 8D and 8E, the biochemical quantification revealed that the TEVG's elastin content of 6.74±3.13 vs. 7.40±0.88 μg/mg, for p=0.7416, and collagen content of 1.78±0.40 vs. 1.81±0.34 μg/mg, for p=0.9297 were equivalent to that of the native ovine IVC.

By one embodiment of the present disclosure, the TEVG samples were analyzed to determine histology and immunochemistry. The explanted TEVG samples are fixed in 10% formalin for 24 hours at 4° C., and thereafter embedded in paraffin. For standard histology, tissue sections are stained with hematoxylin and eosin (H&E), Masson's trichrome, Picrosirius Red, Hart's, and von Kossa stains. For immunohistochemistry, tissue sections were deparaffinized, rehydrated, and blocked for endogenous peroxidase activity and nonspecific staining. The primary antibodies used included: von Willebrand Factor (1:2000, Dako), α-smooth muscle actin (SMA, 1:500, Dako), myosin heavy chain (MHC, 1:500, Abcam), and CD68 (1:200, Abcam). Antibody binding is detected using biotinylated secondary antibodies (Vector), followed by incubation with streptavidinated HRP (Vector). Additionally, development was performed by chromogenic reaction with 3,3-diaminobenzidine (Vector), wherein the nuclei were counterstained with Gill's hematoxylin (Vector).

By one embodiment, lumen diameter, wall thickness, remaining scaffold area, and collagen content are measured from H&E and Picrosirius red (polarized light) staining using the Image J software. It was observed that Pricrosirius red staining revealed collagen fibers. CD68$^+$ macrophages were quantified by analyzing four high-powered fields (HPF, 40×) from a representative section of each sample (n=6) and averaged.

Turning to FIG. 9 is depicted a snapshot 900 illustrating photomicrographs of native IVC and tissue engineered vascular grafts. The tailor-made electro spun fiber TEVG 910 demonstrates well-organized vascular neo-tissue formation over 6 months. Further, it was observed that H&E staining demonstrates extensive cellular infiltration in the TEVG, thereby providing evidence that scaffold parameters such as pore size and fiber diameter permitted host cell infiltration (FIG. 9, part E). All cell-free TEVGs remained patent without complications. Importantly, H&E staining visualized under polarized light microscopy revealed that only 2.09±0.69% of the electro spun fiber scaffold material remained at 6 months, indicating that the vascular neo-tissue is the primary contributor to the biochemical and mechanical properties assessed, further supporting the safety and efficacy of the approach of creating patient-specific grafts as described herein.

On the graft's luminal surface, a cellular monolayer stained positively for vWF confirming successful endothelialization (FIG. 9, part F) like native tissue 920 (FIG. 9, part B). The luminal surfaces displayed no evidence of microthrombosis. Smooth muscle cells are important for vascular function. Accordingly, by one embodiment, mature contractile vascular SMCs are identified using α-SMA (FIG. 9, part G) and MHC markers at 6 months (FIG. 9, part H) in TEVG. A layer of MHC positive cells is circumferentially organized and maintains adequate wall thickness at sub-intimal layers (as shown in FIG. 9, part H). A multilayered population of α-SMA positive cells is primarily present in the neo-media, suggesting that the TEVG may not have been a completely mature neo-IVC at 6 months and that active vascular remodeling is still occurring at this time point (as shown in FIG. 9, part G). Alternatively, α-SMA could indicate synthetic SMCs or myo-fibroblasts, and the α-SMA$^+$/MHC$^-$ staining observed in the TEVG may identify the neo-adventitia or areas of continued growth and remodeling.

Figure 10I:
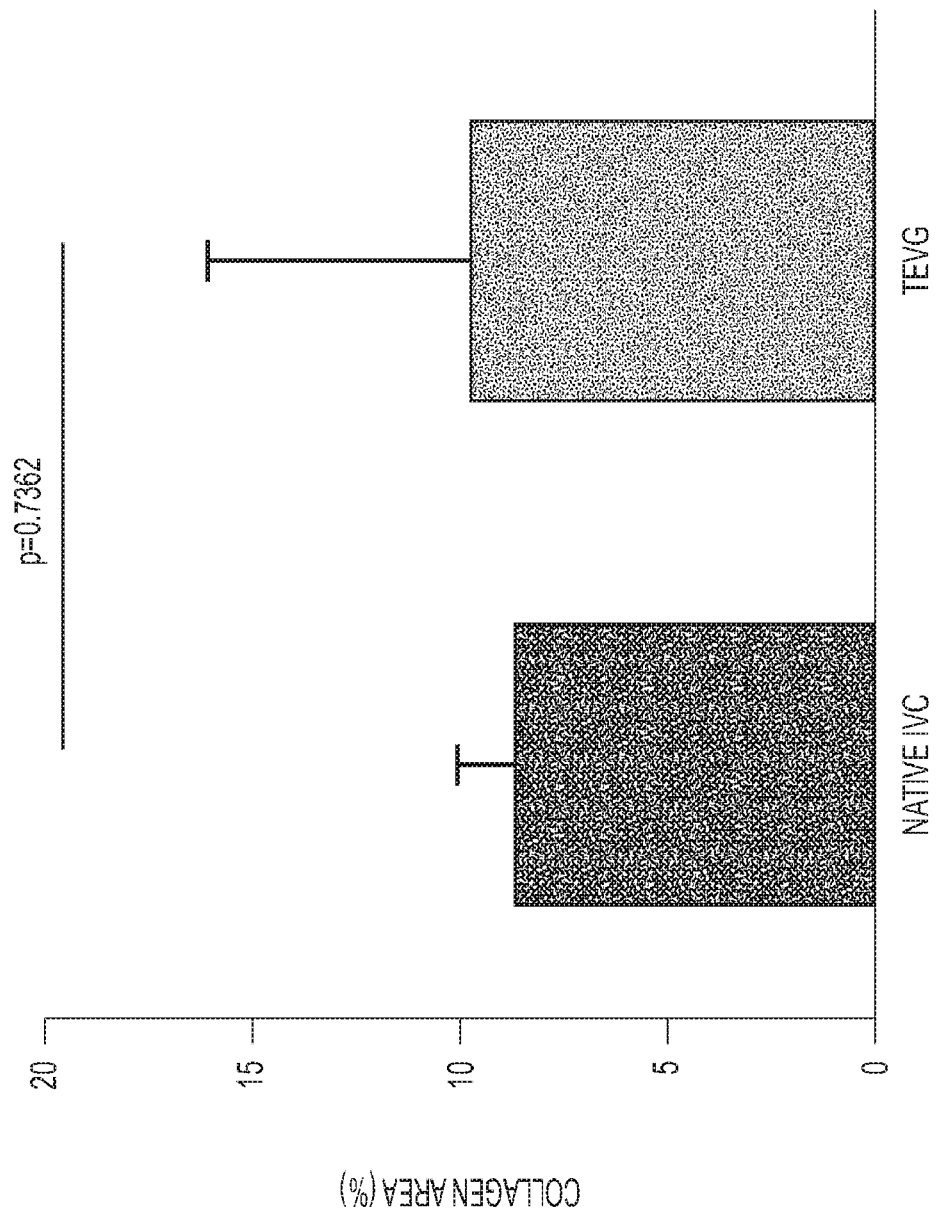
FIG. 10 depicts exemplary snapshots illustrating collagen and elastin deposition in native IVC and tissue engineered vascular grafts.
Figure 12D:
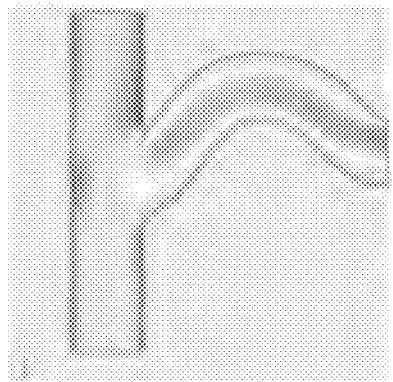
FIG. 12 depicts an exemplary illustration of a patient-specific graft design.
Figure 12E:
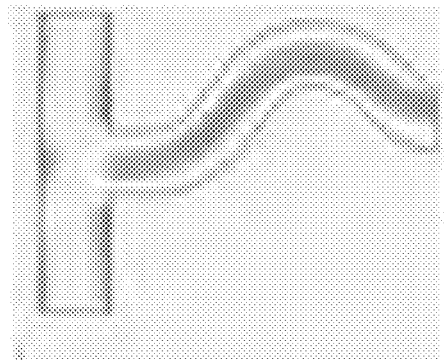
Figure 12B:
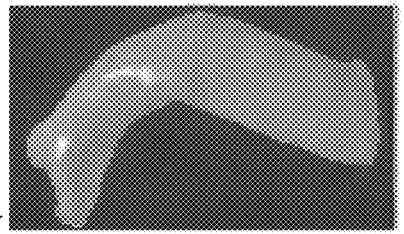
Figure 12C:
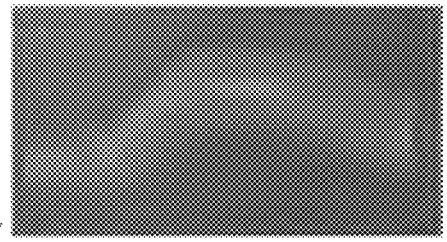
Figure 12A:
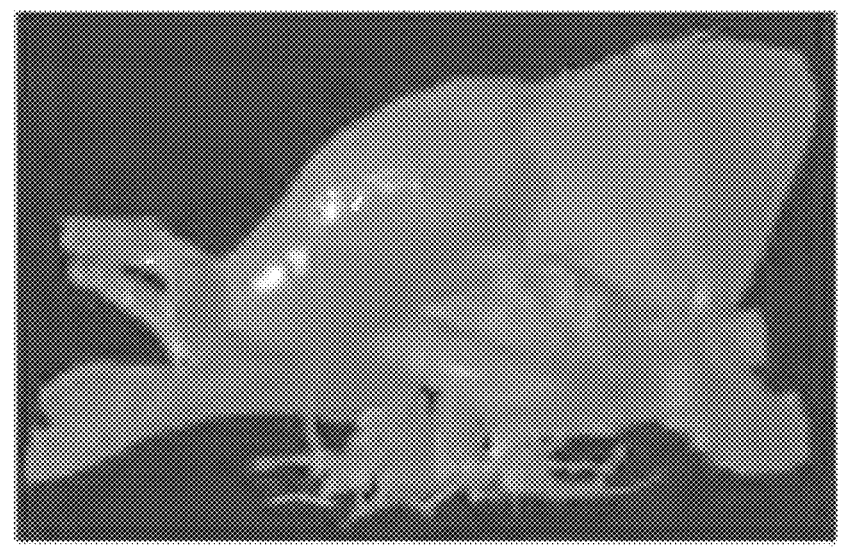

Turning to FIG. 10 is depicted an exemplary snapshot 1000 illustrating collagen and elastin deposition in tissue engineered vascular grafts 1010 and native IVC 1020. Extracellular matrix (ECM) constituents in the TEVG mimicked the circumferential orientation observed in the native IVC. The ECM density in the TEVG (FIG. 9, part E: Picrosirius red, part F: Masson's trichrome) resembled that of native tissue (FIG. 9, part A: Picrosirius red, part B: Masson's trichrome). Collagen deposition, organization, and maturation is confirmed by assessing relative amounts and orientation of thin and thick fibers. The Picrosirius red staining shows that the area fraction of collagen is similar in both the TEVG and native IVC (FIG. 9, part I, a value of 9.75±6.27% vs. a value of 8.75±1.31%, p=0.7362). Hart's staining demonstrates that the elastin composition of the TEVG (FIG. 9, part G) is comparable to that of the native IVC (FIG. 9, part C). Furthermore, it is observed that there is no evidence of ectopic calcification in von Kossa staining at 6 months, as shown in FIG. 9, part D: native IVC, and part F: TEVG.

FIGS. 11A-11C show exemplary illustrations depicting a comparison of wall thickness between native IVC and tissue engineered vascular grafts. By one embodiment, the wall thickness of TEVG is significantly larger than that of native IVC as shown in FIG. 11A (TEVG (N=6) has a value of 2.27±0.91 mm) as compared to native IVC (N=5), which has a value of 0.89±0.15 mm, p=0.0091. It is observed that there is a significant positive correlation between TEVG wall thickness and macrophage infiltration into the scaffold (FIG. 11B, two-tailed Pearson correlation, p=0.0037, $R^2$=0.9020), suggesting that CD68$^+$ macrophages induced inflammation process of vascular remodeling in the graft increased wall thickness of TEVG. Moreover, macrophage infiltration into the TEVGs is assessed by manual quantification of CD68$^+$ cells as shown in FIG. 11C, which is drawn to a scale bar of 20 μm.

According to one embodiment of the present disclosure, an in-vitro experimental evaluation is performed to determine the performance of the patient-specific grafts (manufactured by the process as described in FIG. 4) as compared to surgically implanted grafts. In the experiment, patient data for 10 surgical CDH repairs using vascular graft implants is obtained. Patient data comprises of pre-surgical and post-surgical CT or MRI images and hemodynamics.

Further, vasculature blood volumes on the pre-operative images is isolated and segmented into a 3D model using segmentation software (e.g., Materialize). Extraneous structures are removed, whereafter ideal location for a proximal and distal anastomosis site of the graft is identified. The 3D model is imported into a software package such as CAD, and a new graft is designed to optimally fit the existing vascular anatomy.

By one embodiment, computational fluid dynamic (CFD) analysis is performed to evaluate hemodynamic parameters and optimize the graft design. CFD analysis can be performed by using software such as Autodesk-simulation. A goal in creating the patient-specific grafts is to reduce a pressure differential along a length of the graft while maintaining laminar flow. The design of the graft can be modified to minimize the pressure drop, and in the case of Fontan surgery, the ratio of blood flow to the left and right pulmonary arteries, while maintaining the surgeon-recommended patient age-specific conduit diameter.

In the above experiment, for comparison purposes, the post-operative images (of the surgically implanted grafts) are also isolated and segmented to create replicas of the actual implanted grafts for all 10 patients. The final designed grafts and replicas of the implanted grafts are further converted to STL file format and exported for 3D printing of the mandrel out of stainless steel, such that electrospun electro spun fiber can be deposited onto the mandrel.

Referring to FIG. 12 is depicted an example of a patient-specific graph design 1200. In FIG. 12, part A, depicts a 3D heart model obtained using a post-operative CT/MRI scan of a patient after Fontan surgery. In parts B and C, is depicted an isolated model of the surgically implanted graft and a custom designed graft, respectively. In part D of FIG. 12 is depicted a CFD analysis of the surgically implanted graft, which shows an uneven flow distribution between left and right pulmonary artery. In contrast, as shown in part E of FIG. 12, the CFD analysis of the patient-specific designed graft shows an even flow distribution. Accordingly, by one embodiment, the patient-specific 3D printed grafts as described by embodiments of the present disclosure, incur the advantageous ability of achieving the same mechanical properties as straight grafts, and moreover outperform the surgically implanted grafts in-vitro.

Figure 13:
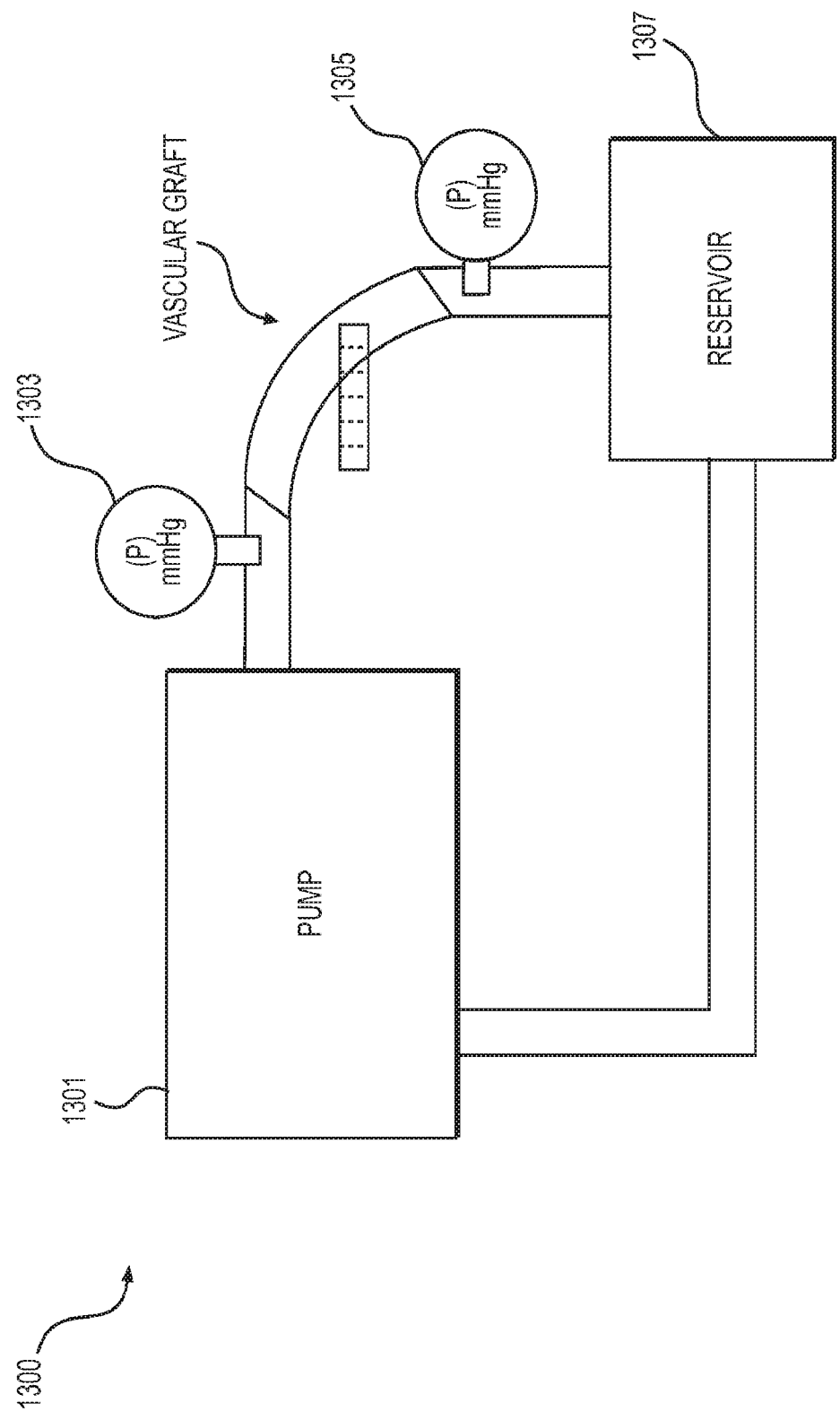
FIG. 13 depicts an exemplary pulsatile flow-loop schematic for pressure drop testing.

By one embodiment of the present disclosure, a pulsatile flow loop schematic 1300 as shown in FIG. 13 is used to test is one can accurately model and predict hemodynamic function of the implant after surgery. As shown in FIG. 13, the grafts are sutured to transparent PVC tubing of similar diameter. The tubing is connected to a pump 1301 and a reservoir 1307 through standard tubing connectors and adapters.

Further, digital pressure gauges (1303 and 1305, respectively), are positioned approximately at a distance of 3 cm from the proximal and distal site of the anastomosis. For each graft, the pump 1301 is set to the hemodynamic parameters of the patient per the case study. The pressure gauges 1303 and 1305 are used to determine the average pressure drop during both systole and diastole over 5 minutes. This process is repeated for at least 4 samples for each case. Using the 10 replicas of the surgically implanted grafts in the flow loop, one can fine-tune the initial and boundary conditions for the CFD analysis, to create a good match between pressure drops observed in the flow loop, CFD models, and post-surgical hemodynamics data.

The results of the above described embodiments validate the efficacy of patient-specific, cell-free electro spun fiber TEVGs created by CAD modeling, 3D-printing, and electrospinning. The patient-specific TEVG is comparable to a native IVC in terms of mechanical testing, angiography, histology, and immunohistochemistry. Serial angiography revealed that the initial PG between the cell-free, patient-specific TEVG and native IVC gradually resolved during the study's 6 month-time course as the scaffold was resorbed. Additionally, the mechanical profile of the TEVG resembled that of the native IVC by the study end point.

With the advances in 3D-printing technologies, tissue-engineering applications are integrating with the fields of regenerative and translational medicine. Although efforts have produced biological blood vessels, the construct's mechanical properties are insufficient unless the tissue is further cultured for maturation. 3D-printing TEVG scaffolds as described herein provide a feasible option for streamlining the process of creating a patient-specific conduit.

The TEVG possesses adequate mechanical properties capable of supporting vascular tissue growth both in-vitro and in-vivo. Moreover, in the above-described embodiments, FDA approved materials with a known degradation profile, a 3D-printed mandrel, and electrospinning to produce custom TEVGs that could transition faster to the clinic. Furthermore, as stated previously, the electrospinning technique used to generate the TVEGs, is advantageous in that it is a highly tunable process by which a wide variety of polymer types and fiber sizes can be spun into various shape of mandrels, thus allowing for the rational design of custom made scaffolds for tissue engineering.

The current "one-size-fits-all" paradigm inadequately addresses the variable and complex anatomies present in the CHD population. Specifically, patient-specific TEVGs are useful for patients with SVAs who undergo extra-cardiac total cavopulmonary connections (ECTCPC). The electro spun fiber construct evaluated in this report promotes autologous vessel growth with the potential of overcoming concerns associated with more rigid materials, such as flow and diameter mismatch. Patient-specific grafts can also avoid the need to offset superior vena cava (SVC) positioning in patients with limited implantation space due to anatomical restrictions. Therefore, the patient-specific TEVG provides immense potential to provide improved clinical and surgical outcomes.

Figure 14:
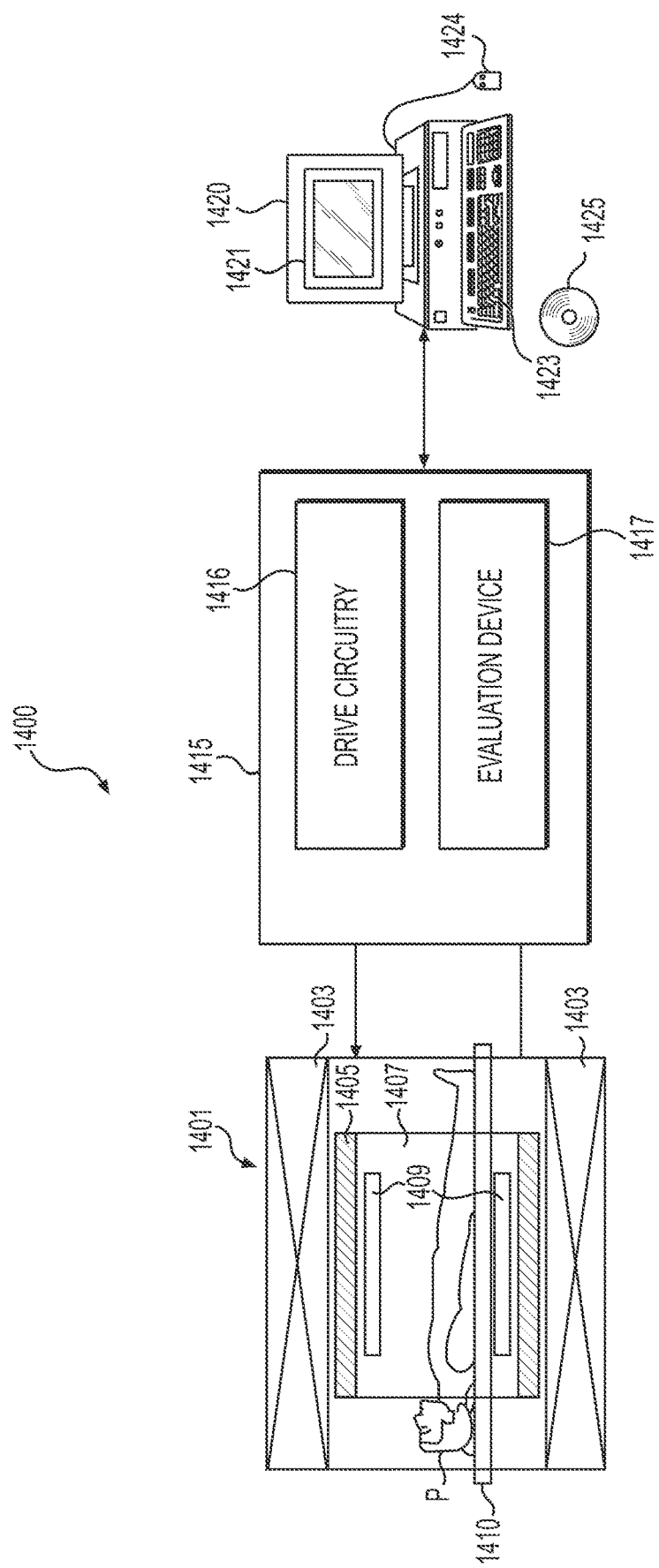
FIG. 14 schematically illustrates an example of a magnetic resonance system.

FIG. 14 schematically illustrates one embodiment of a magnetic resonance system 1400. The magnetic resonance system 1400 may be utilized to capture 3D MRI images of patient-specific anatomy. The magnetic resonance system 1400 includes a tomograph 1401 having a basic field magnet unit 1403, and a gradient system 1405, by which a magnetic field including a gradient field used for magnetic resonance (MR) examination is generated in a measurement chamber 1407. The magnetic resonance system 1400 also includes a send/receive device 1409 for sending high frequency (HF) excitation pulses and capturing echo signals, a table 1410, a controller 1415, by which the tomograph 1401 is controlled and raw data is acquired by the tomograph 1401, and a terminal 1420 connected to the controller 1415.

The controller 1415 includes a drive circuitry 1416 and an evaluation device 1417. During the production of an image data set, echo signals are acquired by the tomograph 1401 from the send and receive device 1409 that is configured as a high-frequency antenna. The tomograph 1401 and the table 1410 are driven by the drive circuitry 1416 such that MR data is acquired in an imaging region that is situated inside the body of a patient P lying on the table 1410.

The evaluation device 1417 acquires the captured echo signals as raw data and stores and processes the raw data. For example, the evaluation device 1417 employs reconstruction to process the raw data that is read out, such that the processed raw data may be represented graphically on a display unit 1421 (e.g., on a screen 1421) of the terminal 1420, and images produced according to one or more of the present embodiments are displayed. In addition to the graphical representation of the image data reconstructed from the raw data, a user, when using the terminal 1420, which in addition to the screen 1421, includes an input device such as, for example a keyboard 1423 and/or a computer mouse 1424, may predetermine a three-dimensional volume section that is to be measured as an imaging region and define further parameters for carrying out the method according to one or more of the present embodiments. The software for the controller 1415 may be loaded into the controller 1415 via the terminal 1420. The software for the controller 1415 may also execute one of the methods of the present embodiments. In one embodiment, one of the methods according to one or more of the present embodiments is contained in a piece of software that runs in the terminal 1420. Regardless of which software the method is contained in, the software may be stored on an electronically readable data medium (e.g., a non-transitory computer-readable storage medium) such as, for example, a DVD 1425 e.g., the software may be read by the terminal 1420 from the DVD 1425 and may be copied either into the controller 1415 or into a computing unit of the terminal 1420, as described next with reference to FIG. 15.

Each of the functions of the described embodiments may be implemented by one or more processing circuits. A processing circuit includes a programmed processor (for example, processor 1503 in FIG. 15), as a processor includes circuitry. A processing circuit also includes devices such as an application-specific integrated circuit (ASIC) and circuit components that are arranged to perform the recited functions.

Figure 15:
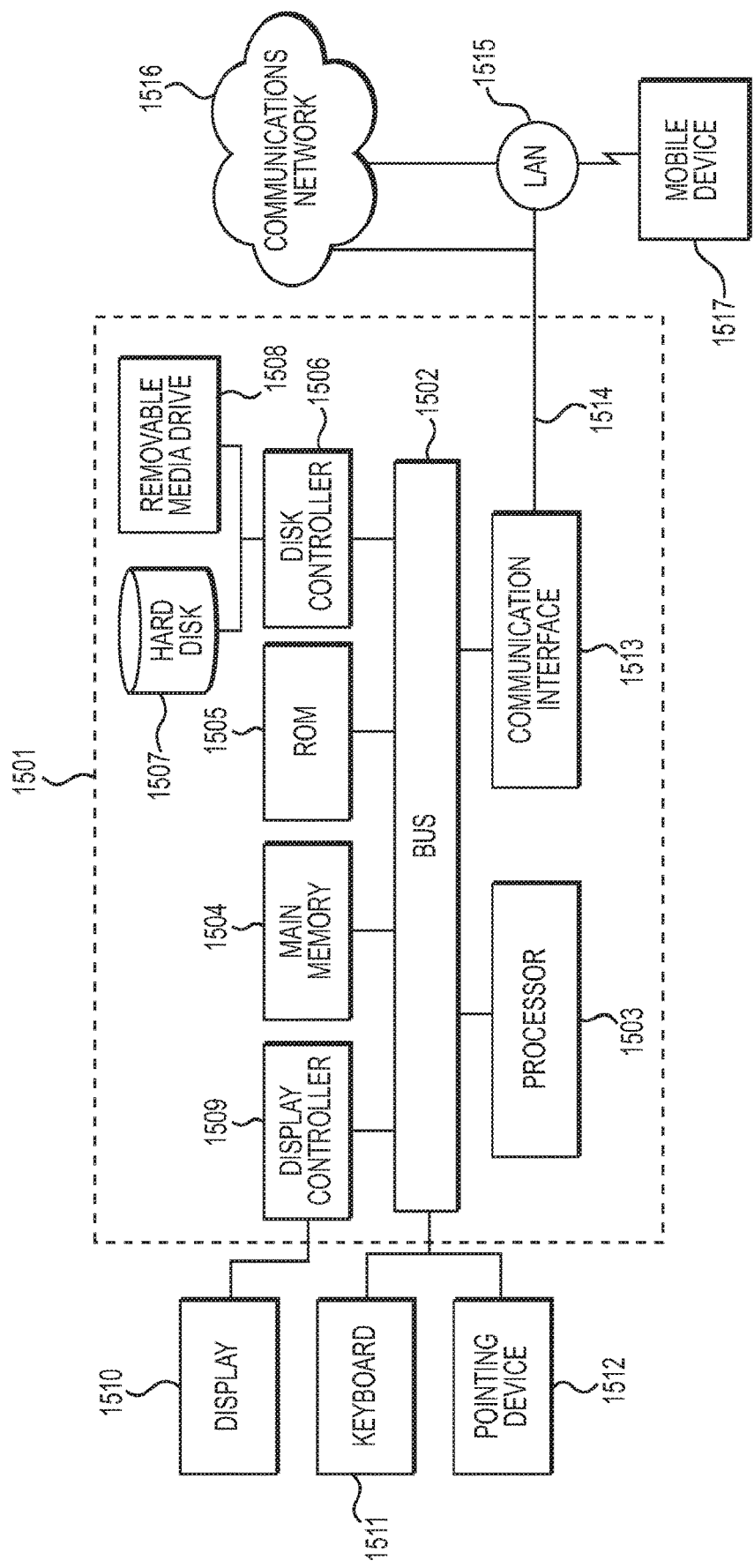
FIG. 15 illustrates a block diagram of a computing device according to one embodiment.

The various features discussed above may be implemented by a computer system (or programmable logic). FIG. 15 illustrates such a computer system 1501. In one embodiment, the computer system 1501 is a particular, special-purpose machine when the processor 1503 is programmed to perform the functions described in the above embodiments.

The computer system 1501 includes a disk controller 1506 coupled to the bus 1502 to control one or more storage devices for storing information and instructions, such as a magnetic hard disk 1507, and a removable media drive 1508 (e.g., floppy disk drive, read-only compact disc drive, read/write compact disc drive, compact disc jukebox, tape drive, and removable magneto-optical drive). The storage devices may be added to the computer system 1501 using an appropriate device interface (e.g., small computer system interface (SCSI), integrated device electronics (IDE), enhanced-IDE (E-IDE), direct memory access (DMA), or ultra-DMA).

The computer system 1501 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1501 may also include a display controller 1509 coupled to the bus 1502 to control a display 1510, for displaying information to a computer user. The computer system includes input devices, such as a keyboard 1511 and a pointing device 1512, for interacting with a computer user and providing information to the processor 1503. The pointing device 1512, for example, may be a mouse, a trackball, a finger for a touch screen sensor, or a pointing stick for communicating direction information and command selections to the processor 1503 and for controlling cursor movement on the display 1510.

The processor 1503 executes one or more sequences of one or more instructions contained in a memory, such as the main memory 1504. Such instructions may be read into the main memory 1504 from another computer readable medium, such as a hard disk 1507 or a removable media drive 1508. One or more processors in a multi-processing arrangement may also be employed to execute the sequences of instructions contained in main memory 1504. In alternative embodiments, hard-wired circuitry may be used in place of or in combination with software instructions. Thus, embodiments are not limited to any specific combination of hardware circuitry and software.

As stated above, the computer system 1501 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1501, for driving a device or devices for implementing the features of the present disclosure, and for enabling the computer system 1501 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term 'computer readable medium' as used herein refers to any non-transitory medium that participates in providing instructions to the processor 1503 for execution. A computer readable medium may take many forms, including but not limited to, non-volatile media or volatile media. Non-volatile media includes, for example, optical, magnetic disks, and magneto-optical disks, such as the hard disk 1507 or the removable media drive 1508. Volatile media includes dynamic memory, such as the main memory 1504. Transmission media, on the contrary, includes coaxial cables, copper wire and fiber optics, including the wires that make up the bus 1502. Transmission media also may also take the form of acoustic or light waves, such as those generated during radio wave and infrared data communications.

Various forms of computer readable media may be involved in carrying out one or more sequences of one or more instructions to processor 1503 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1501 may receive the data on the telephone line and place the data on the bus 1502. The bus 1502 carries the data to the main memory 1504, from which the processor 1503 retrieves and executes the instructions. The instructions received by the main memory 1504 may optionally be stored on storage device 1507 or 1508 either before or after execution by processor 1503.

The computer system 1501 also includes a communication interface 1513 coupled to the bus 1502. The communication interface 1513 provides a two-way data communication coupling to a network link 1514 that is connected to, for example, a local area network (LAN) 1515, or to another communications network 1516 such as the Internet. For example, the communication interface 1513 may be a network interface card to attach to any packet switched LAN. As another example, the communication interface 1513 may be an integrated services digital network (ISDN) card. Wireless links may also be implemented. In any such implementation, the communication interface 1513 sends and receives electrical, electromagnetic or optical signals that carry digital data streams representing various types of information.

The network link 1514 typically provides data communication through one or more networks to other data devices. For example, the network link 1514 may provide a connection to another computer through a local network 1515 (e.g., a LAN) or through equipment operated by a service provider, which provides communication services through a communications network 1516. The local network 1514 and the communications network 1516 use, for example, electrical, electromagnetic, or optical signals that carry digital data streams, and the associated physical layer (e.g., CAT 5 cable, coaxial cable, optical fiber, etc.). The signals through the various networks and the signals on the network link 1514 and through the communication interface 1513, which carry the digital data to and from the computer system 1501 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1501 can transmit and receive data, including program code, through the network(s) 1515 and 1516, the network link 1514 and the communication interface 1513. Moreover, the network link 1514 may provide a connection through a LAN 1515 to a mobile device 1517 such as a personal digital assistant (PDA) laptop computer, or cellular telephone.

While aspects of the present disclosure have been described in conjunction with the specific embodiments thereof that are proposed as examples, alternatives, modifications, and variations to the examples may be made. It should be noted that, as used in the specification and the appended claims, the singular forms "a," "an," and "the" include plural referents unless the context clearly dictates otherwise.

The invention claimed is:

1. A method for generating an electro spun fiber medical implant, comprising:
generating a digital implant model based on dimensions of the electro spun fiber medical implant corresponding to a portion of anatomy of a patient, the dimensions being determined via medical imaging;
applying one or more fluid flow simulations to the digital implant model;
updating the digital implant model based on the applying the one or more fluid flow simulations to the digital implant model;
generating a mandrel model by inverting the digital implant model;
generating a mandrel based on the mandrel model, the mandrel including at least one electrically conductive material therein; and
applying an electrospinning process to the mandrel to generate the electro spun fiber medical implant which circumscribes the mandrel, wherein
the mandrel is removable from within the electro spun fiber medical implant after a disassembly process, and
the digital implant model includes one or more solid areas and one or more void areas encompassed within the one or more solid areas.

2. The method according to claim 1, wherein the electro spun fiber medical implant is a patient-specific electro spun fiber tissue engineered vascular graft (TEVG) based on the portion of anatomy of the patient.

3. The method according to claim 1, wherein the generating the mandrel further comprises printing the mandrel using a 3D printer.

4. The method according to claim 1, wherein the mandrel is composed of several interlocking pieces that disconnect during the disassembly process.

5. The method according to claim 1, wherein the mandrel includes more than one electrically conductive material therein.

6. The method according to claim 1, wherein the mandrel including at least one electrically conductive material on the surface thereof.

7. The method according to claim 1, wherein the electrically conductive material is disposed at varying locations within or on the mandrel resulting in a conductivity gradient across the mandrel.

8. The method according to claim 7, wherein the applying the electrospinning process to the mandrel further comprises applying the electrospinning process to the mandrel to generate the electro spun fiber medical implant which circumscribes the mandrel and which has electro spun fiber deposited in a concentrated fashion in different areas of the electro spun fiber medical implant.

9. The method according to claim 1, wherein the applying the one or more fluid flow simulations to the digital implant model further comprises:
evaluating a blood pressure differential along a length of the electro spun fiber medical implant.

* * * * *

UNITED STATES PATENT AND TRADEMARK OFFICE
CERTIFICATE OF CORRECTION

PATENT NO. : 10,895,020 B2  
APPLICATION NO. : 15/755149  
DATED : January 19, 2021  
INVENTOR(S) : Axel Krieger et al.

Page 1 of 1

It is certified that error appears in the above-identified patent and that said Letters Patent is hereby corrected as shown below:

In the Specification

Column 1, Line 4, Below Title insert:  
--STATEMENT REGARDING FEDERALLY SPONSORED RESEARCH OR DEVELOPMENT  
This invention was made with government support under Grant Number U54 HL119810 awarded by the National Institutes of Health. The government has certain rights in the invention.--, as a new paragraph.

Signed and Sealed this  
First Day of October, 2024

Katherine Kelly Vidal  
*Director of the United States Patent and Trademark Office*